United States Patent
Freyne et al.

(10) Patent No.: US 6,894,046 B2
(45) Date of Patent: May 17, 2005

(54) IL-5 INHIBITING 6-AZAURACIL DERIVATIVES

(75) Inventors: Eddy Jean Edgard Freyne, Rumst (BE); Jean Fernand Armand Lacrampe, Le Mesnil-Esnard (FR); Frederik Dirk Deroose, Drongen (BE); Marc Gaston Venet, Le Mesnil-Esnard (FR)

(73) Assignee: Janssen Pharmaceutica N.V. (BE)

( * ) Notice: Subject to any disclaimer, the term of this patent is extended or adjusted under 35 U.S.C. 154(b) by 0 days.

(21) Appl. No.: 09/812,731

(22) Filed: Mar. 19, 2001

(65) Prior Publication Data

US 2002/0010177 A1 Jan. 24, 2002

Related U.S. Application Data

(63) Continuation of application No. PCT/EP99/06776, filed on Sep. 14, 1999.

(30) Foreign Application Priority Data

Sep. 18, 1998 (EP) .............................................. 98203148

(51) Int. Cl.$^7$ ....................... A61K 31/53; C07D 253/07

(52) U.S. Cl. ................. 514/242; 514/236.2; 514/227.8; 544/182; 544/112; 544/58.6

(58) Field of Search ................. 544/182, 112, 544/58.6; 514/242, 236.2, 227.8

(56) References Cited

U.S. PATENT DOCUMENTS

| | | | |
|---|---|---|---|
| 4,631,278 A | 12/1986 | Boeckx et al. | 514/242 |
| 4,767,760 A | 8/1988 | Boeckx et al. | 514/242 |

FOREIGN PATENT DOCUMENTS

| | | |
|---|---|---|
| EP | 0170316 B1 | 2/1986 |
| EP | 0232932 B1 | 8/1987 |
| EP | 0737672 A2 | 10/1996 |
| EP | 0831088 A1 | 3/1998 |
| WO | WO 99/02504 A1 | 1/1999 |
| WO | WO 99/02505 A1 | 1/1999 |
| WO | WO 00/17195 A1 | 3/2000 |

OTHER PUBLICATIONS

Miller et al., Chemical Abstracts, vol. 92:51708 (1980).*
Miller, My;Lari, Howes, Jr., Lynch, Lynch, Koch, Anticoccidial Derivatives of 6–Azauracil, 2, High Potency and Long Plasma Life of N1–Phenyl Structures, Journal of Medicinal Chemistry, Pfizer Medical Research Laboratories, Groton, CT, 1979, vol. 22, No. 12, 1483–1487.
PCT International Search Report dated Jan. 19, 2000 for PCT Appln. No. PCT/EP99/06776 which relates to U.S. Patent Appln. No. 09/812,731.
Castro, et al., "Reactifs De Couplage Pepidique IV (1)–L'Hexafluorophosphate De Benzotriazolyl N–Oxytrusdimethylamino Phosphonium (B.O.P.)." *Tetrahedron Letters*, 1975, pp. 1219–1222, No. 14.
Baggiolini, et al., "CC Chemokines in Allergic Inflammation." *Immunology Today*, 1994, pp. 127–133, vol. 15, No. 3.
Carr et al., "Monocyte Chemoattractant Protein 1 Acts As A T–Lymphocyte Chemoattractant." *Proc. Natl. Acad. Sci., USA, Immunology*, 1994, pp. 3652–3656, vol. 91.

* cited by examiner

Primary Examiner—Richard L. Raymond
(74) Attorney, Agent, or Firm—Gabriel Lopez; Alana G. Kriegeman

(57) ABSTRACT

The present invention is concerned with the compounds of formula

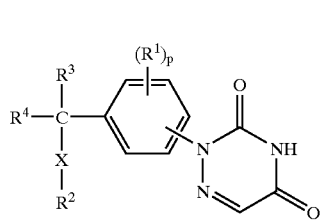

(I)

the N-oxides, the pharmaceutically acceptable addition salts and the stereochemically isomeric forms thereof, wherein p is 0 to 4; X is O, S, $NR^5$ or a direct bond; Y is O, S, $NR^5$ or $S(O)_2$; $R^1$ independently is $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, $Het^3$, $R^6$, $NR^7R^8$ or substituted $C_{1-4}$alkyl; $R^2$ is $Het^1$, $C_{3-7}$cycloalkyl or optionally substituted $C_{1-6}$alkyl and if X is O, S or $NR^5$, then $R^2$ may also represent aminocarbonyl, aminothiocarbonyl, $C_{1-4}$alkylcarbonyl, $C_{1-4}$alkylthiocarbonyl, arylcarbonyl, arylthiocarbonyl, $Het^1$carbonyl or $Het^1$thiocarbonyl; $R^3$ and $R^4$ independently are hydrogen, $C_{1-6}$alkyl or $C_{3-7}$cycloalkyl; $R^3$ and $R^4$ form a $C_{2-6}$alkanediyl; $R^5$ is hydrogen or $C_{1-4}$alkyl; $R^6$ is a sulfonyl or sulfinyl derivative; $R^7$ and $R^8$ are independently hydrogen, optionally substituted $C_{1-4}$alkyl, aryl, a carbonyl containing moiety, $C_{3-7}$cycloalkyl, $-Y-C_{1-4}$alkanediyl-C(=O)-O-$R^{14}$, $Het^3$, $Het^4$ and $R^6$; $R^{11}$ is hydroxy, mercapto, cyano, nitro, halo, trihalomethyl, $C_{1-4}$alkyloxy, formyl, trihalo$C_{1-4}$alkylsulfonyloxy, $R^6$, $NR^7R^8$, C(=O)$NR^7R^8$, $C_{1-4}$alkanediyl-C(=O)-O-$R^{14}$, -C(=O)-O-$R^{14}$, $-Y-C_{1-4}$alkanediyl-C(=O)-O-$R^{14}$, aryl, aryloxy, arylcarbonyl, $C_{3-7}$cycloalkyl, $C_{3-7}$cycloalkyloxy, phthalimide-2-yl, $Het^3$ and C(=O)$Het^3$; $R^{14}$ is hydrogen, $C_{1-4}$alkyl, $C_{3-7}$cycloalkyl, aminocarbonylmethylene or mono- or di($C_{1-4}$alkyl)aminocarbonylmethylene; aryl is optionally substituted phenyl; $Het^1$, $Het^2$, $Het^3$ and $Het^4$ are optionally substituted heterocycles; to processes for their preparation and compositions comprising them. It further relates to their use as a medicine.

59 Claims, No Drawings

IL-5 INHIBITING 6-AZAURACIL DERIVATIVES

CROSS REFERENCE TO RELATED APPLICATIONS

This application is a continuation application of PCT/EP99/06776, filed Sep. 14, 1999 which application claims priority from EP 98203148.6, filed Sep. 18, 1998.

The present invention concerns IL-5 inhibiting 6-azauracil derivatives useful for treating eosinophil-dependent inflammatory diseases; to processes for their preparation and compositions comprising them. It further relates to their use as a medicine.

Eosinophil influx, leading to subsequent tissue damage, is an important pathogenic event in bronchial asthma and allergic diseases. The cytokine interleukin-5 (IL-5), produced mainly by T lymphocytes as a glycoprotein, induces the differentiation of eosinophils in bone marrow and, primes eosinophils for activation in peripheral blood and sustains their survival in tissues. As such, IL-5 plays a critical role in the process of eosinophilic inflammation. Hence, the possibility that inhibitors of IL-5 production would reduce the production, activation and/or survival of eosinophils provides a therapeutic approach to the treatment of bronchial asthma and allergic diseases such as, atopic dermatitis, allergic rhinitis, allergic conjunctivitis, and also other eosinophil-dependent inflammatory diseases.

Steroids, which strongly inhibit IL-5 production in vitro, have long been used as the only drugs with remarkable efficacy for bronchial asthma and atopic dermatitis, but they cause various serious adverse reactions such as diabetes, hypertension and cataracts. Therefore, it would be desirable to find non-steroidal compounds having the ability to inhibit IL-5 production in human T-cells and which have little or no adverse reactions.

U.S. Pat. No. 4,631,278 discloses α-aryl-4-(4,5-dihydro-3,5-dioxo-1,2,4-triazine-2(3H)-yl)-benzeneacetonitriles and U.S. Pat. No. 4,767,760 discloses 2-(substituted phenyl)-1,2,4-triazine-3,5(2H,4H)-diones, all having anti-protozoal activity, in particular, anti-coccidial activity. EP 831,088 discloses 1,2,4-triazine-3,5-diones as anticoccidial agents and EP 737,672 discloses a method of preparing such compounds. Miller et al. (J. Med. Chem., 1979, 22(12), p1483–1487) disclose anticoccidial derivatives of 6-azauracil.

Unexpectedly, the 6-azauracil derivatives of the present invention prove to be potent inhibitors of the production of IL-5.

The present invention is concerned with the compounds of formula

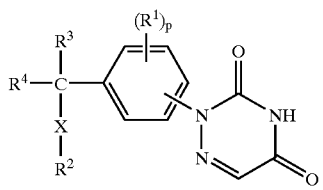

(I)

the N-oxides, the pharmaceutically acceptable addition salts and the stereochemically isomeric forms thereof, wherein:
p represents an integer being 0, 1, 2, 3 or 4;
X represents O, S, NR$^5$ or a direct bond;
Y represents O, S, NR$^5$, or S(O)$_2$;

each R$^1$ independently represents $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, Het$^3$, R$^6$, NR$^7$R$^8$ or $C_{1-4}$alkyl substituted with Het$^3$, R$^6$ or NR$^7$R$^8$;

R$^2$ represents Het$^1$, $C_{3-7}$cycloalkyl, $C_{1-6}$alkyl or $C_{1-6}$alkyl substituted with one or two substituents selected from hydroxy, cyano, amino, mono- or di($C_{1-4}$alkyl)amino, $C_{1-6}$alkyloxy, $C_{1-6}$alkylsulfonyloxy, $C_{1-6}$alkyloxycarbonyl, $C_{3-7}$cycloalkyl, aryl, aryloxy, arylthio, Het$^1$, Het$^1$oxy and Het$^1$thio; and if X is O, S or NR$^5$, then R$^2$ may also represent aminocarbonyl, aminothiocarbonyl, $C_{1-4}$alkylcarbonyl, $C_{1-4}$alkylthiocarbonyl, arylcarbonyl, arylthiocarbonyl, Het$^1$carbonyl or Het$^1$thiocarbonyl;

R$^3$ represents hydrogen, $C_{1-6}$alkyl or $C_{3-7}$Cycloalkyl;
R$^4$ represents hydrogen, $C_{1-6}$alkyl or $C_{3-7}$cycloalkyl; or
R$^3$ and R$^4$ taken together form a $C_{2-6}$alkanediyl;
R$^5$ represents hydrogen or $C_{1-4}$alkyl;

each R$^6$ independently represents $C_{1-6}$alkylsulfonyl, aminosulfonyl, mono- or di-($C_{1-4}$alkyl)aminosulfonyl, mono- or di(benzyl)aminosulfonyl, polyhalo-$C_{1-6}$alkylsulfonyl, $C_{1-6}$alkylsulfinyl, phenyl$C_{1-4}$alkylsulfonyl, piperazinylsulfonyl, aminopiperidinylsulfonyl, piperidinylaminosulfonyl, N-$C_{1-4}$alkyl-N-piperidinylamino-sulfonyl or mono- or di($C_{1-4}$alkyl)amino$C_{1-4}$alkylsulfonyl;

each R$^7$ and each R$^8$ are independently selected from hydrogen, $C_{1-4}$alkyl, hydroxy-$C_{1-4}$alkyl, dihydroxy$C_{1-4}$ alkyl, aryl, aryl$C_{1-4}$alkyl, $C_{1-4}$alkyloxy$C_{1-4}$alkyl, $C_{1-4}$alkyl-carbonyl, aminocarbonyl, arylcarbonyl, Het$^3$carbonyl, $C_{1-4}$alkylcarbonyloxy-$C_{1-4}$alkyl-carbonyl, hydroxy$C_{1-4}$ alkylcarbonyl, $C_{1-4}$alkyloxycarbonylcarbonyl, mono- or di($C_{1-4}$alkyl)amino$C_{1-4}$alkyl, arylaminocarbonyl, arylaminothiocarbonyl, Het$^3$amino-carbonyl, Het$^3$aminothiocarbonyl, $C_{3-7}$cycloalkyl, pyridinyl$C_{1-4}$alkyl, $C_{1-4}$alkanediyl-C(=O)—O—R$^{14}$, —C(=O)—O—R$^{14}$, —Y—$C_{1-4}$alkanediyl-C(=O)—O—R$^{14}$, Het$^3$, Het$^4$ and R$^6$;

R$^9$ and R$^{10}$ are each independently selected from hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$ alkyl, $C_{1-4}$alkylcarbonyl, aminocarbonyl, phenylcarbonyl, Het$^3$carbonyl, $C_{1-4}$alkylcarbonyloxy$C_{1-4}$alkylcarbonyl, hydroxy$C_{1-4}$ alkylcarbonyl, $C_{1-4}$alkyloxycarbonylcarbonyl, mono- or di($C_{1-4}$alkyl)-amino$C_{1-4}$alkyl, phenylaminocarbonyl, phenylaminothiocarbonyl, Het$^3$aminocarbonyl, Het$^3$aminothiocarbonyl, $C_{3-7}$cycloalkyl, pyridinyl$C_{1-4}$alkyl, $C_{1-4}$alkanediyl-C(=O)—O—R$^{14}$, —C(=O)—O—R$^{14}$, —Y—$C_{1-4}$alkanediyl-C(=O)—O—R$^{14}$, Het$^3$, Het$^4$ and R$^6$;

each R$^{11}$ independently being selected from hydroxy, mercapto, cyano, nitro, halo, trihalomethyl, $C_{1-4}$alkyloxy, formyl, trihalo$C_{1-4}$alkylsulfonyloxy, R$^6$, NR$^7$R$^8$, C(=O)NR$^7$R$^8$, —C(=O)—O—R$^{14}$, —Y—$C_{1-4}$alkanediyl-C(=O)—O—R$^{14}$, aryl, aryloxy, arylcarbonyl, $C_{3-7}$cycloalkyl, $C_{3-7}$cycloalkyloxy, phthalimide-2-yl, Het$^3$ and C(=O)Het$^3$;

R$^{12}$ and R$^{13}$ are each independently selected from hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$ alkyl, $C_{1-4}$alkylcarbonyl, phenylcarbonyl, $C_{1-4}$alkylcarbonyloxy$C_{1-4}$alkylcarbonyl, hydroxy$C_{1-4}$alkylcarbonyl, $C_{1-4}$alkyloxycarbonylcarbonyl, mono- or di($C_{1-4}$alkyl)amino$C_{1-4}$alkyl, phenylaminocarbonyl, carbonyl, phenylaminothiocarbonyl, $C_{3-7}$cycloalkyl, pyridinyl$C_{1-4}$alkyl, $C_{1-4}$alkanediyl-C(=O)—O—$R^{14}$, —C(=O)—O—$R^{14}$, —Y—$C_{1-4}$alkanediyl-C(=O)—O—$R^{14}$ and $R^6$;

each $R^{14}$ independently represents hydrogen, $C_{1-4}$alkyl, $C_{3-7}$cycloalkyl, aminocarbonylmethylene or mono- or di($C_{1-4}$alkyl)aminocarbonylmethylene;

aryl represents phenyl optionally substituted with one, two or three substituents each independently selected from nitro, azido, cyano, halo, hydroxy, $C_{1-4}$alkyl, $C_{3-7}$cycloalkyl, $C_{1-4}$alkyloxy, formyl, polyhalo$C_{1-4}$alkyl, $NR^9R^{10}$, C(=O)$NR^9R^{10}$, C(=O)—O—$R^{14}$, $R^6$, —O—$R^6$, phenyl, $Het^3$, C(=O)$Het^3$ and $C_{1-4}$alkyl substituted with hydroxy, $C_{1-4}$alkyloxy, C(=O)—O—$R^{14}$, —Y—$C_{1-4}$alkanediyl-C(=O)—O—$R^{14}$, $Het^3$ or $NR^9R^{10}$;

$Het^1$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thioxanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from $Het^2$, $R^{11}$ and $C_{1-4}$alkyl optionally substituted with one or two substituents independently selected from $Het^2$ and $R^{11}$;

$Het^2$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from $Het^4$, $R^{11}$ and $C_{1-4}$alkyl optionally substituted with one or two substituents independently selected from $Het^4$ and $R^{11}$;

$Het^3$ represents a monocyclic heterocycle selected from pyrrolidinyl, piperidinyl, piperazinyl, morpholinyl, thiomorpholinyl and tetrahydropyranyl; wherein said monocyclic heterocycles each independently may optionally be substituted with, where possible, one, two, three or four substituents each independently selected from hydroxy, $C_{1-4}$alkyl, $C_{1-4}$alkyloxy, $C_{1-4}$alkylcarbonyl, piperidinyl, $NR^{12}R^{13}$, C(=O)—O—$R^{14}$, $R^6$ and $C_{1-4}$alkyl substituted with one or two substituents independently selected from hydroxy, $C_{1-4}$alkyloxy, phenyl, C(=O)—O—$R^{14}$, —Y—$C_{1-4}$alkanediyl-C(=O)—O—$R^{14}$, $R^6$ and $NR^{12}R^{13}$;

$Het^4$ represents a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl.

As used in the foregoing definitions and hereinafter, halo is generic to fluoro, chloro, bromo and iodo; $C_{3-7}$cycloalkyl is generic to cyclopropyl, cyclobutyl, cyclopentyl, cyclohexyl and cycloheptyl; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{1-6}$alkyl is meant to include $C_{1-4}$alkyl and the higher homologues thereof having 5 or 6 carbon atoms such as, for example, pentyl, 2-methylbutyl, hexyl, 2-methylpentyl and the like; polyhalo$C_{1-4}$alkyl is defined as polyhalosubstituted $C_{1-4}$alkyl, in particular $C_{1-4}$alkyl substituted with 1 to 6 halogen atoms, more in particular bromomethyl, chloromethyl, difluoro- or trifluoromethyl; polyhalo$C_{1-6}$alkyl is defined as polyhalosubstituted $C_{1-6}$alkyl. The term $C_{1-4}$alkanediyl defines bivalent straight or branch chained alkanediyl radicals having from 1 to 4 carbon atoms such as, for example, methylene, 1,2-ethanediyl, 1,3-propanediyl, 1,4-butanediyl and the like: $C_{2-6}$alkanediyl defines bivalent straight or branch chained alkanediyl radicals having from 2 to 6 carbon atoms such as, for example, 1,2-ethanediyl, 1,3-propanediyl, 1,4-butanediyl, 1,5-pentanediyl, 1,6-hexanediyl and the like.

$Het^1$, $Het^2$, $Het^3$ and $Het^4$ are meant to include all the possible isomeric forms of the heterocycles mentioned in the definition of $Het^1$, $Het^2$, $Het^3$ and $Het^4$, for instance, pyrtolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl.

The heterocycles represented by $Het^1$, $Het^2$, $Het^3$ and $Het^4$ may be attached to the remainder of the molecule of formula (I) through any ring carbon or heteroatom as appropriate. Thus, for example, when the heterocycle is imidazolyl, it may be a 1-imidazolyl, 2-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl; when it is benzthiazolyl, it may be 2-benzthiazolyl, 4-benzthiazolyl, 5-benzthiazolyl, 6-benzthiazolyl and 7-benzthiazolyl.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, ethanedioic, propanedioic, butanedioic, (Z)-2-butenedioic, (E)-2-butenedioic, 2-hydroxybutanedioic, 2,3- dihydroxybutanedioic, 2-hydroxy-1,2,3-propanetricarboxylic, methanesulfonic, ethanesulfonic, benzene-sulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The N-oxide forms of the present compounds are meant to comprise the compounds of formula (I) wherein one or several nitrogen atoms are oxidized to the so-called N-oxide. For example, one or more nitrogen atoms of any of the heterocycles in the definition of $Het^1$, $Het^2$ and $Het^3$ may be N-oxidized.

Some of the compounds of formula (I) may also exist in their tautomeric forms. Such forms although not explicitly indicated in the above formula are intended to be included within the scope of the present invention. For example, a hydroxy substituted triazine moiety may also exist as the corresponding triazinone; a hydroxy substituted pyrimidine moiety may also exist as the corresponding pyrimidinone.

The term "stereochemically isomeric forms" as used hereinbefore defines all the possible stereoisomeric forms in which the compounds of formula (I) can exist. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration, used herein in accordance with Chemical Abstracts nomenclature. Stereochemically isomeric forms of the compounds of formula (I) are obviously intended to be embraced within the scope of this invention.

The compounds of formula (I) and some of the intermediates in the present invention contain one or more asymmetric carbon atoms. The pure and mixed stereochemically isomeric forms of the compounds of formula (I) are intended to be embraced within the scope of the present invention.

Whenever used hereinafter, the term "compounds of formula (I)" is meant to also include their N-oxide forms, their pharmaceutically acceptable addition salts, and their stereochemically isomeric forms.

Suitably, each $R^7$ and each $R^8$ are independently selected from hydrogen, $C_{1-4}$alkyl, hydroxy$C_{1-4}$alkyl, dihydroxy$C_{1-4}$alkyl, aryl, aryl$C_{1-4}$alkyl, $C_{1-4}$alkyloxy$C_{1-4}$alkyl, $C_{1-4}$alkylcarbonyl aminocarbonyl, arylcarbonyl, $Het^3$carbonyl, $C_{1-4}$alkylcarbonyloxy-$C_{1-4}$alkyl-carbonyl, hydroxy$C_{1-4}$alkylcarbonyl, $C_{1-4}$alkyloxycarbonylcarbonyl, mono- or di($C_{1-4}$alkyl)amino$C_{1-4}$alkyl, arylaminocarbonyl, arylaminothiocarbonyl, $Het^3$amino-carbonyl, $Het^3$aminothiocarbonyl, $C_{3-7}$cycloalkyl, pyridinyl$C_{1-4}$alkyl, $C_{1-4}$alkanediyl-C(=O)—O—$R^{14}$, —C(=O)—O—$R^{14}$, —Y—$C_{1-4}$alkanediyl-C(=O)—O—$R^{1-4}$, $Het^3$ and $R^6$; $R^9$ and $R^{10}$ are each independently selected from hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$alkyl, $C_{1-4}$alkylcarbonyl, aminocarbonyl, phenylcarbonyl, $Het^3$carbonyl, $C_{1-4}$alkylcarbonyloxy$C_{1-4}$alkylcarbonyl, hydroxy$C_{1-4}$alkylcarbonyl, $C_{1-4}$alkyloxycarbonylcarbonyl, mono- or di($C_{1-4}$alkyl)amino-$C_{1-4}$alkyl, phenylaminocarbonyl, phenylaminothiocarbonyl, $Het^3$aminocarbonyl, $Het^3$aminothiocarbonyl, $C_{3-7}$cycloalkyl, pyridinyl$C_{1-4}$alkyl, $C_{1-4}$alkanediyl-C(=O)—O—$R^{14}$, —C(=O)—O—$R^{14}$, —Y—$C_{1-4}$alkanediyl-C(=O)—O—$R^{14}$, $Het^3$ and $R^6$;

$R^{11}$ is being selected from hydroxy, mercapto, cyano, nitro, halo, trihalomethyl, $C_{1-4}$alkyloxy, formyl, trihalo$C_{1-4}$alkylsulfonyloxy, $R^6$, $NR^7R^8$, C(=O)$NR^7R^8$, —C(=O)—O—$R^{14}$, —Y—$C_{1-4}$alkanediyl-C(=O)—O—$R^{14}$, aryl, aryloxy, arylcarbonyl, $C_{3-7}$cycloalkyl, $C_{3-7}$cycloalkyloxy, phthalimide-2-yl, $Het^3$, $Het^4$ and C(=O)$Het^3$; and $Het^2$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from $R^{11}$ and $C_{1-4}$alkyl optionally substituted with one or two substituents independently selected from $R^{11}$.

An interesting group of compounds are those compounds of formula (I) wherein the 6-azauracil moiety is connected to the phenyl ring in the para or meta position relative to the carbon atom bearing the —X—$R^2$, $R^3$ and $R^4$ substituents; preferably in the para position.

Another interesting group contains those compounds of formula (I) wherein one or more of the following restrictions apply:

p is 0, 1 or 2; more in particular p is 2;

X is S, $NR^5$, or a direct bond; more in particular NH or a direct bond;

each $R^1$ independently is halo, polyhalo$C_{1-4}$alkyl, $C_{1-4}$alkyl, $C_{1-6}$alkyloxy or aryl, preferably, chloro or trifluoromethyl, more preferably chloro;

$R^2$ is $Het^1$ or $C_{1-6}$alkyl substituted with one or two substituents selected from hydroxy, cyano, amino, mono- or di($C_{1-4}$alkyl)amino, $C_{1-6}$alkyloxy, $C_{1-6}$alkylsulfonyloxy, $C_{1-6}$alkyloxycarbonyl, $C_{3-7}$cycloalkyl, aryl, aryloxy, arylthio, $Het^1$, $Het^1$oxy and $Het^1$thio; and if X is O, S or $NR^5$, then $R^2$ may also represent aminocarbonyl, aminothiocarbonyl, $C_{1-4}$alkylcarbonyl, $C_{1-4}$alkylthiocarbonyl, arylcarbonyl, arylthiocarbonyl, $Het^1$carbonyl or $Het^1$thiocarbonyl; particularly $R^2$ is $Het^1$, $C_{1-6}$alkyl substituted with two substituents selected from cyano, aryl, $Het^1$ and $Het^1$thio; or in the event X is NH, $R^2$ may also be aminothiocarbonyl or $Het^1$carbonyl;

$R^3$ is hydrogen, methyl, ethyl, propyl or cyclohexyl; preferably, methyl;

$R^4$ is hydrogen or methyl; preferably, methyl;

$R^3$ and $R^4$ are taken together to form a 1,4-butanediyl;

$R^6$ is $C_{1-6}$alkylsulfonyl, mono- or di($C_{1-4}$alkyl) aminosulfonyl or aminosulfonyl;

$R^7$ and $R^8$ are each independently hydrogen, $C_{1-4}$alkyl, Het$^3$ or $R^6$;

$R^9$ and $R^{10}$ are each independently hydrogen, $C_{1-4}$alkyloxy$C_{1-4}$alkyl, $C_{1-4}$alkylcarbonyl, aminocarbonyl, Het$^3$carbonyl, Het$^3$, Het$^4$ or $R^6$;

$R^{11}$ is hydroxy, cyano, nitro, halo, $C_{1-4}$alkyloxy, formyl, $NR^7R^8$, $C(=O)NR^7R^8$, $-C(=O)-O-R^{14}$, aryl, arylcarbonyl, Het$^3$ and $C(=O)$Het$^3$;

$R^{14}$ is hydrogen or $C_{1-4}$alkyl;

aryl is phenyl optionally substituted with one, two or three substituents each independently selected from nitro, cyano, halo, hydroxy, $C_{1-4}$alkyl, $C_{3-7}$cycloalkyl, $C_{1-4}$alkyloxy, formyl, polyhalo$C_{1-4}$alkyl, $NR^9R^{10}$, $C(=O)NR^9R^{10}$, $C(=O)-O-R^{14}$, $-O-R^6$, phenyl, $C(=O)$Het$^3$ and $C_{1-4}$alkyl substituted with hydroxy, $C_{1-4}$alkyloxy, $C(=O)-O-R^{14}$, Het$^3$ or $NR^9R^{10}$;

Het$^1$ is a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, in particular imidazolyl, oxadiazolyl, thiazolyl, pyrimidinyl or pyridinyl, wherein said monocyclic heterocycles each independently may optionally be substituted with one, or where possible, two or three substituents each independently selected from Het$^2$, $R^{11}$ and $C_{1-4}$alkyl optionally substituted with Het$^2$ or $R^{11}$; preferably Het$^1$ is imidazolyl, oxadiazolyl, thiazolyl, pyrimidinyl or pyridinyl each independently and optionally substituted with one, or where possible, two or three substituents each independently selected from Het$^2$, $R^{11}$ and $C_{1-4}$alkyl optionally substituted with Het$^2$ or $R^{11}$;

Het$^2$ is an aromatic heterocycle; more in particular furanyl, thienyl, pyridinyl or benzothienyl, wherein said aromatic heterocycles each independently may optionally be substituted with one, or where possible, two or three substituents each independently selected from Het$^4$, $R^{11}$ and $C_{1-4}$alkyl optionally substituted with $R^{11}$;

Het$^3$ is piperidinyl, piperazinyl, morpholinyl and tetrahydropyranyl each independently and optionally substituted with, where possible, one, two, three or four substituents each independently selected from hydroxy, $C_{1-4}$alkyl, $C(=O)-O-R^{14}$, $C_{1-4}$alkylcarbonyl, $R^6$, piperidinyl and $C_{1-4}$alkyl substituted with one or two substituents independently selected from hydroxy, $C_{1-4}$alkyloxy, $C(=O)-O-R^{14}$ and phenyl;

Het$^4$ is thienyl or pyridinyl.

Suitably, the compounds of formula (I) contain an ester function such as those defined in $C_{1-4}$alkyloxycarbonyl and $C(=O)-O-R^{14}$.

Special compounds are those compounds of formula (I) wherein p is 1 or 2 and each $R^1$ is chloro, in particular p is 2 and both $R^1$ substituents are chloro; more preferably the two chloro substituents are in the ortho positions relative to the carbon atom bearing the $-X-R^2$, $R^3$ and $R^4$ substituents.

Other special groups of compounds are those compounds wherein $R^3$ and $R^4$ each independently are $C_{1-6}$alkyl or $C_{3-7}$cycloalkyl; or those compounds wherein Het$^1$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from Het$^2$, $R^{11}$ and $C_{1-4}$alkyl optionally substituted with one or two substituents independently selected from Het$^2$ and $R^{11}$; provided Het$^1$ is other than 2-substituted-pyridin-3-yl; or the compounds of formula (I) provided that those compounds wherein X is a direct bond, at least one of $R^3$ and $R^4$ is hydrogen, and $R^2$ is 3-pyridinyl optionally substituted in the 6 position with an optionally substituted alkyl or acyl group are excluded.

Particular compounds are those compounds of formula (I) wherein the 6-azauracil moiety is in the para position relative to the carbon atom bearing the $-X-R^2$, $R^3$ and $R^4$ substituents, and p is 2 whereby both $R^1$ substituents are chloro positioned ortho relative to the carbon atom bearing the $-X-R^2$, $R^3$ and $R^4$ substituents.

Other particular compounds are those compounds of formula (I) wherein X is a direct bond and $R^2$ is a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, in particular imidazolyl, oxadiazolyl, thiazolyl, pyrimidinyl or pyridinyl, wherein said monocyclic heterocycles each independently may optionally be substituted with one, or where possible, two or three substituents each independently selected from Het$^2$, $R^{11}$ and $C_{1-4}$alkyl optionally substituted with Het$^2$ or $R^{11}$; more in particular $R^2$ is optionally substituted thiazolyl, pyridinyl or oxadiazolyl.

Preferred compounds are those compounds of formula (I) wherein $R^3$ and $R^4$ are both methyl and $-X-R^2$ is Het$^1$ wherein Het$^1$ suitably is optionally substituted thiazolyl, pyridinyl or oxadiazolyl.

More preferred compounds are those compounds of formula (I) wherein $R^3$ and $R^4$ are both methyl, $-X-R^2$ is optionally substituted 2-thiazolyl or 3-oxadiazolyl, the 6-azauracil moiety is in the para position relative to the carbon atom bearing the $-X-R^2$, $R^3$ and $R^4$ substituents, and p is 2 whereby both $R^1$ substituents are chloro positioned ortho relative to the carbon atom bearing the $-X-R^2$, $R^3$ and $R^4$ substituents.

Most preferred compounds are

2-[3,5-dichloro-4-[1-methyl-1-(4-phenyl-2-thiazolyl) ethyl]phenyl]-1,2,4-triazine-3,5(2H,4H)-dione;

2-[3,5-dichloro-4-[1-[4-(3-chlorophenyl)-5-methyl-2-thiazolyl]-1-methylethyl]phenyl]-1,2,4-triazine-3,5(2H,4H)-dione;

2-[3,5-dichloro-4-[1-methyl-1-(5-phenyl-1,2,4-oxadiazol-3-yl)ethyl]phenyl]-1,2,4-triazine-3,5(2H,4H)-dione;

2-[3,5-dichloro-4-[1-(4,5-diphenyl-2-thiazolyl)-1-methylethyl]phenyl]-1,2,4-triazine-3,5(2H,4H)-dione;

2-[3,5-dichloro-4-[1-methyl-1-[5-(2-methylphenyl)-1,2,4-oxadiazol-3-yl]ethyl]phenyl]-1,2,4-triazine-3,5(2H,4H)-dione;

2-[3,5-dichloro-4-[1-methyl-1-(4-methyl-5-phenyl-2-thiazolyl)ethyl]phenyl]-1,2,4-triazine-3,5(2H,4H)-dione;

2-[3,5-dichloro-4-[1-methyl-1-[4-phenyl-5-(3-pyridinyl)-2-thiazolyl]ethyl]phenyl]-1,2,4-triazine-3,5(2H,4H)-dione;

2-[3,5-dichloro-4-[1-methyl-1-[4-phenyl-5-(phenylmethyl)-2-thiazolyl]ethyl]phenyl]-1,2,4-triazine-3,5(2H,4H)-dione;

2-[3,5-dichloro-4-[1-methyl-1-[5-(4-pyridinyl)-1,2,4-oxadiazol-3-yl]ethyl]phenyl]-1,2,4-triazine-3,5(2H,4H)-dione;

2-[3,5-dichloro-4-[1-methyl-1-[4-(3-thienyl)-2-thiazolyl]ethyl]phenyl]-1,2,4-triazine-3,5(2H,4H)-dione;

2-[3,5-dichloro-4-[1-[4-(2-furanyl)-2-thiazolyl]-1-methylethyl]phenyl]-1,2,4-triazine-3,5(2H,4H)-dione;

2-[3,5-dichloro-4-[1-methyl-1-[5-(3-pyridinyl)-1,2,4-oxadiazol-3-yl]ethyl]phenyl]-1,2,4-triazine-3,5(2H,4H)-dione;

2-[3,5-dichloro-4-[1-methyl-1-[5-(2-methyl-3-pyridinyl)-1,2,4-oxadiazol-3-yl]ethyl]phenyl]-1,2,4-triazine-3,5(2H,4H)-dione;

2-[3,5-dichloro-4-[1-methyl-1-(5-phenyl-1,3,4-oxadiazol-2-yl)ethyl]phenyl]-1,2,4-triazine-3,5(2H,4H)-dione; the N-oxides, the pharmaceutically acceptable addition salts and the stereochemically isomeric forms thereof.

In order to simplify the structural representation of the compounds of formula (I), the group

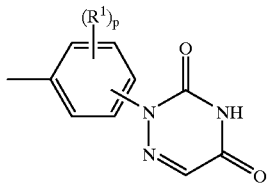

will hereinafter be represented by the symbol D.

Compounds of formula (I) can generally be prepared by reacting an intermediate of formula (II) wherein $W^1$ is a suitable leaving group such as, for example, a halogen atom, with an appropriate reagent of formula (III).

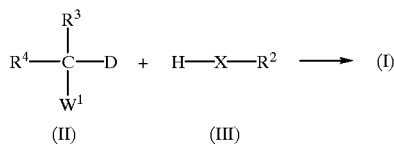

Said reaction may be performed in a reaction-inert solvent such as, for example, acetonitrile, N,N-dimethylformamide, acetic acid, tetrahydrofuran, ethanol or a mixture thereof. Alternatively, in case the reagent of formula (III) acts as a solvent, no additional reaction-inert solvent is required. The reaction is optionally carried out in the presence of a base such as, for example, 1,8-diazabicyclo[5.4.0]undec-7-ene, sodium bicarbonate, sodiumethanolate and the like. Convenient reaction temperatures range between −70° C. and reflux temperature.

In this and the following preparations, the reaction products may be isolated from the reaction medium and, if necessary, further purified according to methodologies generally known in the art such as, for example, extraction, crystallization, distillation, trituration and chromatography.

Some of the compounds and intermediates of the present invention can be prepared according to or analogous to the procedures described in EP-A-0,170,316, EP-A-0,232,932 and PCT/EP98/04191.

For instance, compounds of formula (I) may generally be prepared by cyclizing an intermediate of formula (IV) wherein L is a suitable leaving group such as, for example, $C_{1-6}$alkyloxy or halo, and E represents an appropriate electron attracting group such as, for example, an ester, an amide, a cyanide, $C_{1-6}$alkylsulfonyloxy and the like groups; and eliminating the group E of the thus obtained triazinedione of formula (V). The cyclization can suitably be carried out by refluxing the intermediate (IV) in acidic medium such as acetic acid and in the presence of a base such as, for example, potassium acetate.

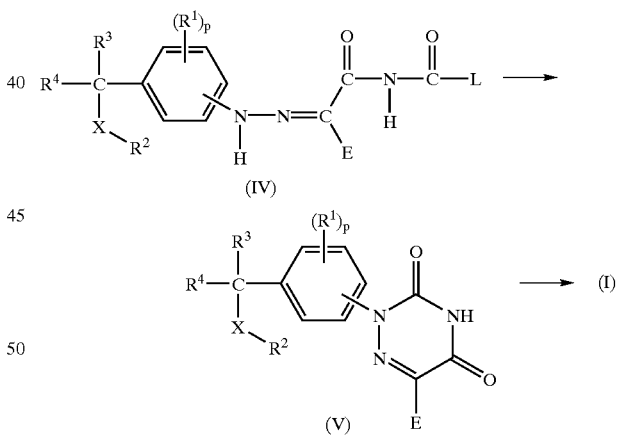

Depending on its nature, E can be eliminated using various art-known elimination procedures. For example when E is an amide or a cyano moiety, it can be hydrolized to a carboxylic moiety by for instance refluxing the intermediate bearing the E group in hydrochloric acid and acetic acid. The thus obtained intermediate can then be further reacted with mercaptoacetic acid or a functional derivative thereof to obtain a compound of formula (I). Said reaction is conveniently carried out at elevated temperatures ranging up to reflux temperature.

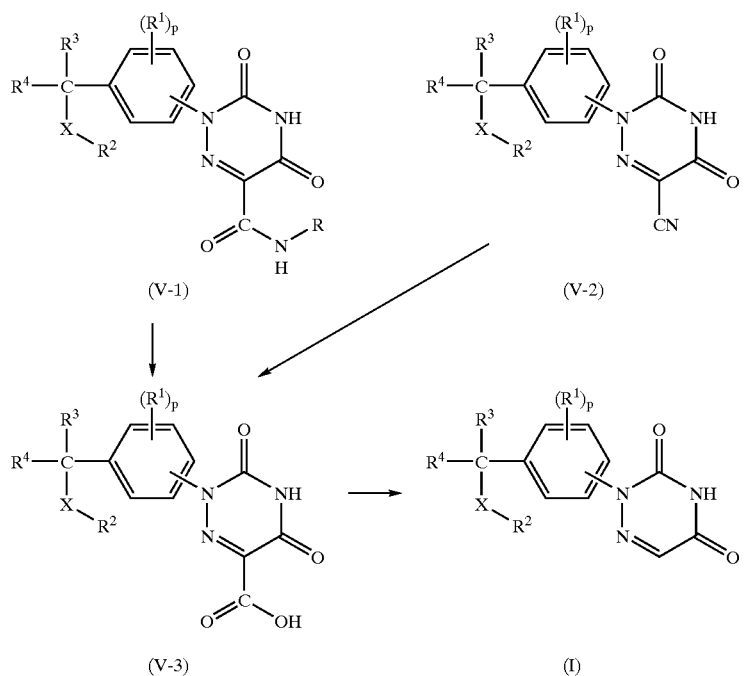

A suitable way to prepare intermediates of formula (IV) involves the reaction of an intermediate of formula (VI) with sodium nitrate or a functional derivative thereof in an acidic medium such as for example hydrochloric acid in acetic acid, and preferably in the same reaction mixture, further reacting the thus obtained intermediate with a reagent of formula (VII) wherein L and E are as defined above, in the presence of a base such as, for example, sodium acetate.

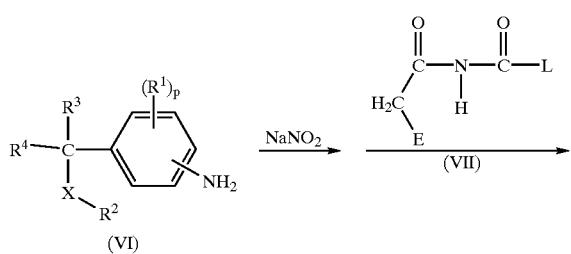

-continued

An interesting subgroup within the present invention are those compounds of formula (I) wherein —X—$R^2$ is an optionally substituted 2-thiazolyl moiety, said compounds being represented by formula (I-a). The optionally substituted 2-thiazolyl moiety can be incorporated in the compounds of formula (I-a) at different stages of the preparation process.

For instance, scheme 1 depicts three possible ways to prepare compounds of formula (I-a).

Scheme 1

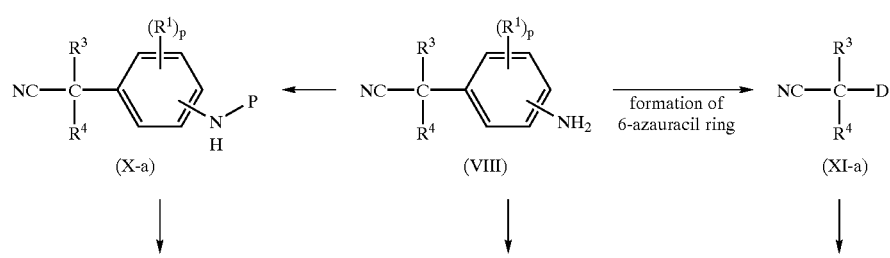

-continued

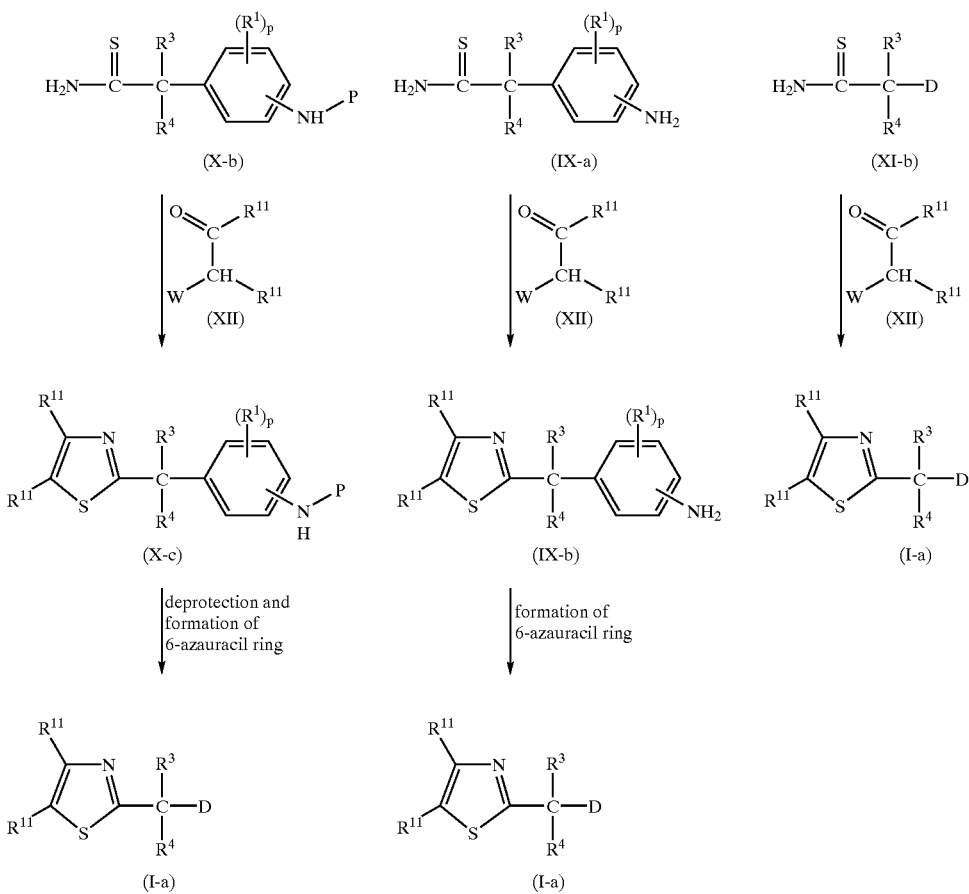

A first pathway involves the reaction of the cyano moiety in an intermediate of formula (VII) to the corresponding thioamide using H$_2$S gas in a suitable solvent such as, for example, pyridine and in the presence of a base such as, for example, triethylamine, thus obtaining an intermediate of formula (IX-a). This thioamide can then be cyclized with an intermediate of formula (XII) wherein W is a suitable leaving group such as, for example, a halogen, e.g. bromo, in a suitable solvent such as, for example, ethanol. The amino moiety in the resulting 2-thiazolyl derivative of formula (IX-b) can then be further reacted as described hereinabove to form a 6-azauracil ring, thus obtaining a compound of formula (I-a).

A second pathway to form compounds of formula (I-a) involves first the protecting of the amino moiety in an intermediate of formula (VIII) by introducing a suitable protective group P such as, for example, an alkylcarbonyl group, using art-known protection techniques. In the example of P being a alkylcarbonyl group, the intermediates of formula (VII) can be reacted with the corresponding anhydride of formula alkyl-C(=O)—O—C(=O)-alkyl in an appropriate solvent such as, for example, toluene. The thus obtained intermediate of formula (X-a) can then be further reacted according to the first pathway described hereinabove. The final step, before formation of the 6-azauracil ring can be initiated after having deprotected the amino moiety using art-known deprotection techniques. In the example of P being a alkylcarbonyl group, the intermediates of formula (X-c) may be deprotected by reacting them in a suitable solvent such as, for example, ethanol, in the presence of an acid such as, for example, hydrochloric acid.

A third pathway involves first the formation of the 6-azauracil ring as described hereinabove but starting from an intermediate of formula (VIII), and subsequently reacting the thus formed intermediate of formula (XI-a) with H$_2$S and further reacting the thioamide of formula (XI-b) with an intermediate of formula (XII) as described in the first pathway, to finally form a compound of formula (I-a).

Another interesting subgroup within the present invention are those compounds of formula (I) wherein —X—R$^2$ is an optionally substituted 1,2,4-oxadiazol-3-yl moiety, said compounds being represented by formula (I-b-1). The optionally substituted 1,2,4-oxadiazol-3-yl moiety can be incorporated at the same stages of the reaction procedure as depicted for the 2-thiazolyl derivatives in scheme 1.

For instance, analogous to one of the three pathways shown in scheme 1, compounds of formula (I-b) can be performed by reacting an intermediate of formula (VIII) as depicted in scheme 2.

Scheme 2

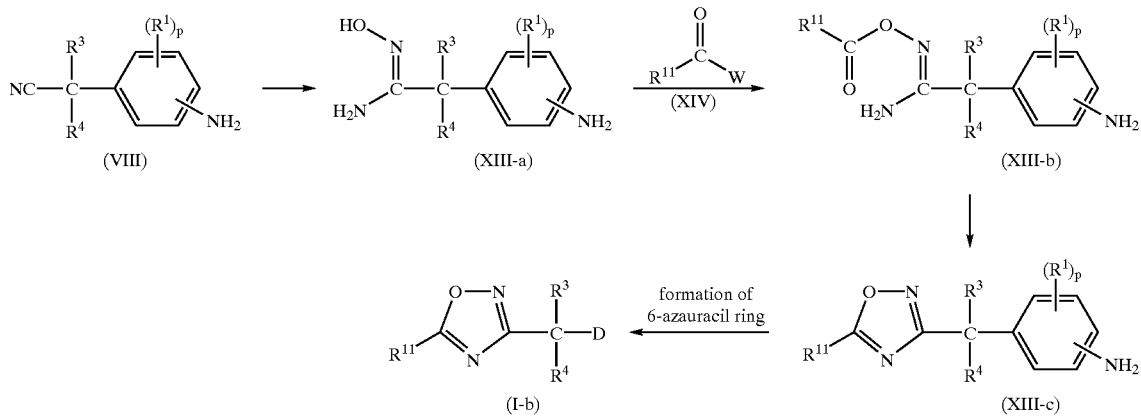

In said scheme 2, the cyano group of an intermediate of formula (VII) is reacted with hydroxylamine or a functional derivative thereof in a suitable solvent such as, for example, methanol, arid in the presence of a base such as, for example sodium methanolate. The thus formed intermediate of formula (XIII-a) is then reacted with an intermediate of formula (XIV) wherein W is a suitable leaving group such as, for example, a halogen, e.g. chloro, in an appropriate solvent such as, for example, dichloromethane, and in the presence Still another interesting subgroup within the present invention are those compounds of formula (I) wherein —X—$R^2$ is an optionally substituted 1,3,4-oxadiazol-2-yl moiety, said compounds being represented by formula (I-b-2).

For instance, compounds of formula (I-b-2) can be prepared as depicted in scheme 3.

Scheme 3

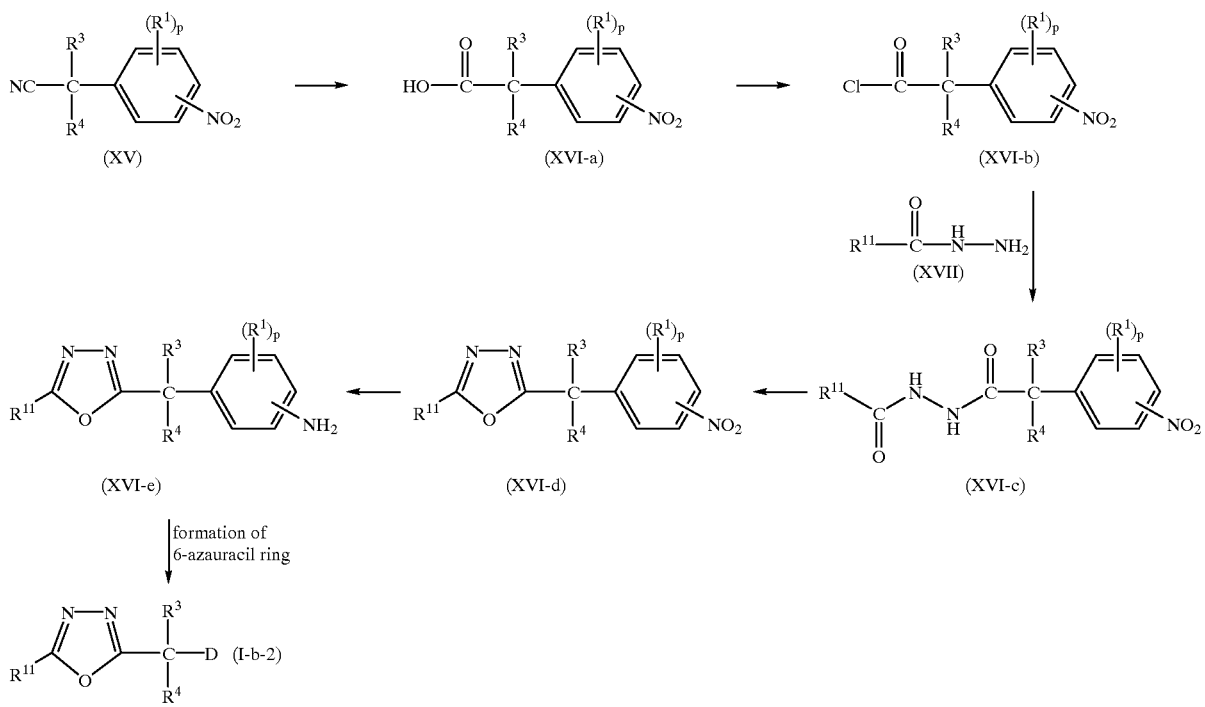

of a base, such as, for example, N,N-(1-methyl-ethyl)ethaneamine. The resulting intermediate of formula (XIII-b) is then cyclized to a 3-oxadiazolyl derivative of formula (XIII-c). The amino moiety in the intermediates of formula (XIII-c) can then be transformed to the 6-azauracil ring as described above.

The nitrile moiety in an intermediate of formula (XV) is transformed into a carboxylic acid moiety using art-known techniques. For instance, the nitrile derivative may be refluxed in a mixture of sulfuric acid and acetic acid in water. The carboxylic acid derivative of formula (XVI-a) may the further be reacted with a chlorinating agent such as, for example, thionyl chloride, to form an acylchloride derivative of formula (XVI-b). Subsequently, The acyl chloride may be reacted with a hydrazine derivative of formula (XVII) in a suitable solvent such as, for example, dichloromethane, and in the presence of a base such as, for example N,N-(1-methylethyl)ethaneamine. The thus formed intermediate of formula (XVI-c) may be cyclized to a 1,2,4-oxadiazol-2-yl derivative of formula (XVI-d) in the presence of phophoryl chloride. As a final step before the formation of the 6-azauracil ring as described above, the nitro group in the intermediates of formula (XVI-e) is reduced to an amino group using art-known reduction techniques such as, for instance, reducing the nitro group with hydrogen in methanol and in the presence of a catalyst such as Raney Nickel.

Yet another interesting subgroup within the present invention are those compounds of formula (I) wherein —X—$R^2$ is —NH—$R^2$, said compounds being represented by formula (I-c-1). Scheme 4 depicts a suitable pathway to obtain compounds of formula (I-c-1).

Scheme 4

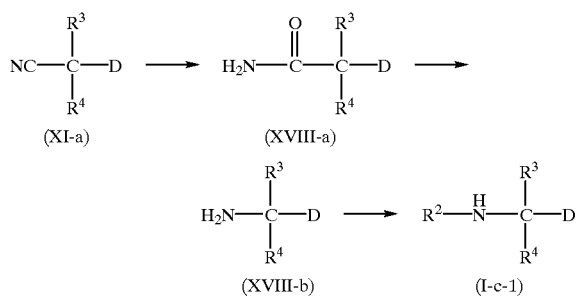

In said scheme 4, the cyano moiety of an intermediate of formula (XI-a) is hydrolized to the corresponding amide using art-known techniques such as, for instance, hydrolysis in the presence of acetic acid and sulfuric acid. The thus formed amide in the intermediates of formula (XVII-a) can be transformed in an amine using (diacetoxy)iodobenzene or a functional derivative thereof in a suitable solvent such as, for example a mixture of water and acetonitrile. The amine derivative of formula (XVIII-b) can then be reacted with benzotriazol-1-yloxytris(dimethylamino) phosphonium hexafluorophosphate as described in Tetrahedron Letters No.14 (1975) 1219–1222 to obtain acylated compounds, or with a functional derivative thereof such as, for instance, an isothiocyanate, in an appropriate solvent such as, for example, tetrahydrofuran.

Intermediates of formula (VIII) can be prepared as depicted in scheme 5.

Scheme 5

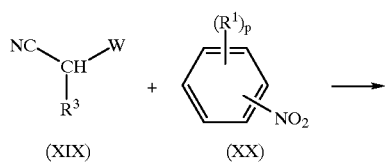

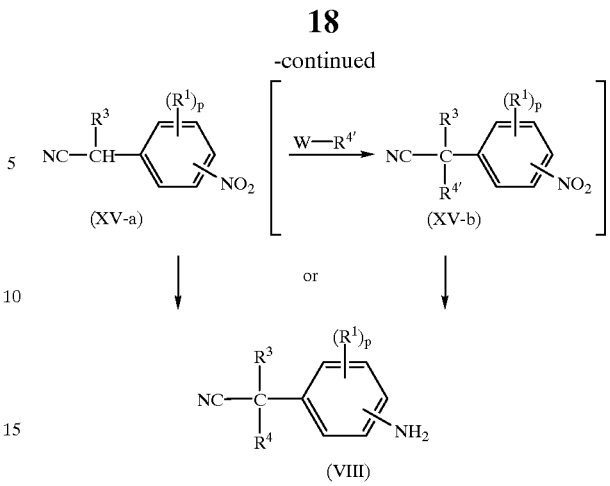

An intermediate of formula (XIX) and an intermediate of formula (XX) may be reacted in a suitable solvent such as, for example, dimethylsulfoxide, in the presence of a base such as, for example sodium hydroxide, to form an intermediate of formula (XV-a). The nitro moiety in the intermediates of formula (XV-a) may either be immediately reduced to an amino group using art-known reduction techniques such as, for example, reducing the nitro group with hydrogen in methanol and in the presence of a catalyst such as Raney Nickel, or may first be reacted with an intermediate of formula $R^{4'}$-W wherein $R^{4'}$ is the same as $R^4$ but other than hydrogen and W is a suitable leaving group such as, for example, a halogen, e.g. iodo, in a suitable solvent such as, for example, N,N-dimethylformamide, and in the presence of a suitable base such as, for example, sodium hydride, before reducing the nitro moiety.

The compounds of formula (I) can also be converted into each other following art-known procedures of functional group transformation such as, for example, those mentioned in PCT/EP98/04191 and the ones exemplified in the experimental part hereinafter.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydro-carbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g. counter-current distribution, liquid chromatography and the like.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures.

IL-5, also known as eosinophil differentiating factor (EDF) or eosinophil colony stimulating factor (Eo-CSF), is a major survival and differentiation factor for eosinophils and therefore thought to be a key player in eosinophil infiltration into tissues. There is ample evidence that eosinophil influx is an important pathogenic event in bronchial asthma and allergic diseases such as, cheilitis, irritable bowel disease, eczema, urticaria, vasculitis, vulvitis, winterfeet, atopic dermatitis, pollinosis, allergic rhinitis and allergic conjunctivitis; and other inflammatory diseases, such as eosinophilic syndrome, allergic angiitis, eosinophilic fasciutis, eosinophilic pneumonia, PIE syndrome, idiopathic eosinophilia, eosinophilic myalgia, Crohn's disease, ulcerative colitis and the like diseases.

The present compounds also inhibit the production of other chemokines such as monocyte chemotactic protein-1 and -3 (MCP-1 and MCP-3). MCP-1 is known to attract both T-cells, in which IL-5 production mainly occurs, and monocytes, which are known to act synergetically with eosinophils (Carr et al., 1994, Immunology, 91, 3652–3656). MCP-3 also plays a primary role in allergic inflammation as it is known to mobilize and activate basophil and eosinophil leukocytes (Baggiolini et al., 1994, Immunology Today, 15(3), 127–133).

The present compounds have no or little effect on the production of other chemokines such as IL-1, IL-2, IL-3, IL-4, IL-6, IL-10, γ-interferon (IFN-γ) and granulocyte-macrophage colony stimulating factor (GM-CSF) indicating that the present IL-5 inhibitors do not act as broad-spectrum immunosuppressives.

The selective chemokine inhibitory effect of the present compounds can be demonstrated by in vitro chemokine measurements in human blood of which the test results for IL-5 are presented in the experimental part hereinafter. In vivo observations such as the inhibition of eosinophilia in mouse ear, the inhibition of blood eosinophilia in the Ascaris mouse model; the reduction of serum IL-5 protein production and splenic IL-5 mRNA expression induced by anti-CD3 antibody in mice and the inhibition of allergen- or Sephadex-induced pulmonary influx of eosinophils in guinea-pig are indicative for the usefulness of the present compounds in the treatment of eosinophil-dependent inflammatory diseases.

The present inhibitors of IL-5 production are orally active compounds.

The intermediates of formula (XI-a) are interesting intermediates. Not only have they a particular usefulness as intermediates in the preparation of the compounds of formula (I), they also have valuable pharmacological activity.

In view of the above pharmacological properties, the compounds of formula (I) can be used as a medicine. In particular, the present compounds can be used in the manufacture of a medicament for treating eosinophil-dependent inflammatory diseases as mentioned hereinabove, more in particular bronchial asthma, atopic dertmatitis, allergic rhinitis and allergic conjunctivitis.

In view of the utility of the compounds of formula (I), there is provided a method of treating warm-blooded animals, including humans, suffering from eosinophil-dependent inflammatory diseases, in particular bronchial asthma, atopic dertmatitis, allergic rhinitis and allergic conjunctivitis. Said method comprises the systemic or topical administration of an effective amount of a compound of formula (I), a N-oxide form, a pharmaceutically acceptable addition salt or a possible stereoisomeric form thereof, to warm-blooded animals, including humans.

The present invention also provides compositions for treating eosinophil-dependent inflammatory diseases comprising a therapeutically effective amount of a compound of formula (I) and a pharmaceutically acceptable carrier or diluent.

To prepare the pharmaceutical compositions of this invention, a therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous, or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellant such as nitrogen, carbon dioxide, a freon, or without a propellant such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In order to enhance the solubility and/or the stability of the compounds of formula (I) in pharmaceutical compositions, it can be advantageous to employ α-, β-, or γ-cyclo-dextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated D-CD; hydroxy$C_{1-6}$alkyl, particularly hydroxyethyl, hydroxypropyl or hydroxybutyl; carboxy$C_{1-6}$alkyl, particularly carboxymethyl or carboxy-ethyl; $C_{1-6}$alkylcarbonyl, particularly acetyl; $C_{1-6}$alkyloxycarbonyl$C_{1-6}$alkyl or carboxy-$C_{1-6}$alkyloxy$C_{1-6}$alkyl, particularly carboxymethoxypropyl or carboxyethoxy-propyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The M.S. value can be determined by various analytical techniques, preferably, as measured by mass spectrometry, the M.S. ranges from 0.125 to 10.

The average substitution degree (D.S.) refers to the average number of substituted hydroxyls per anhydroglucose unit. The D.S. value can be determined by various analytical techniques, preferably, as measured by mass spectrometry, the D.S. ranges from 0.125 to 3.

Due to their high degree of selectivity as IL-5 inhibitors, the compounds of formula (I) as defined above, are also useful to mark or identify receptors. To this purpose, the compounds of the present invention need to be labelled, in particular by replacing, partially or completely, one or more atoms in the molecule by their radioactive isotopes. Examples of interesting labelled compounds are those compounds having at least one halo which is a radioactive isotope of iodine, bromine or fluorine; or those compounds having at least one $^{11}$C-atom or tritium atom.

One particular group consists of those compounds of formula (I) wherein $R^3$ and/or $R^4$ are a radioactive halogen atom. In principle, any compound of formula (I) containing a halogen atom is prone for radiolabelling by replacing the halogen atom by a suitable isotope. Suitable halogen radio-isotopes to this purpose are radioactive iodides, e.g. $^{122}$I, $^{123}$I, $^{125}$I, $^{131}$I; radioactive bromides, e.g. $^{75}$Br, $^{76}$Br, $^{77}$Br and $^{82}$Br, and radioactive fluorides, e.g. $^{18}$F. The introduction of a radioactive halogen atom can be performed by a suitable exchange reaction or by using any one of the procedures as described hereinabove to prepare halogen derivatives of formula (I).

Another interesting form of radiolabelling is by substituting a carbon atom by a $^{11}$C-atom or the substitution of a hydrogen atom by a tritium atom.

Hence, said radiolabelled compounds of formula (I) can be used in a process of specifically marking receptor sites in biological material. Said process comprises the steps of (a) radiolabelling a compound of formula (I), (b) administering this radio-labelled compound to biological material and subsequently (c) detecting the emissions from the radiolabelled compound. The term biological material is meant to comprise every kind of material which has a biological origin. More in particular this term refers to tissue samples, plasma or body fluids but also to animals, specially warm-blooded animals, or parts of animals such as organs.

The radiolabelled compounds of formula (I) are also useful as agents for screening whether a test compound has the ability to occupy or bind to a particular receptor site. The degree to which a test compound will displace a compound of formula (I) from such a particular receptor site will show the test compound ability as either an agonist, an antagonist or a mixed agonist/antagonist of said receptor.

When used in in vivo assays, the radiolabelled compounds are administered in an appropriate composition to an animal and the location of said radiolabelled compounds is detected using imaging techniques, such as, for instance, Single Photon Emission Computerized Tomography (SPECT) or Positron Emission Tomography (PETI) and the like. In this manner the distribution of the particular receptor sites throughout the body can be detected and organs containing said receptor sites can be visualized by the imaging techniques mentioned hereinabove. This process of imaging an organ by administering a radiolabelled compound of formula (I) and detecting the emissions from the radioactive compound also constitutes a part of the present invention.

In general, it is contemplated that a therapeutically effective daily amount would be from 0.01 mg/kg to 50 mg/kg body weight, in particular from 0.05 mg/kg to 10 mg/kg body weight. A method of treatment may also include administering the active ingredient on a regimen of between two or four intakes per day.

Experimental Part

In the examples hereinafter, "DMSO" stands for dimethylsulfoxide, "RT" stands for room temperature, "DMF" stand for N,N-dimethylformamide, "EtOAc" stands for ethylacetate, "DIPE" stands for diisopropylether and "THF" stands for tetrahydrofuran.

A. Preparation of the Intermediate Compounds

EXAMPLE A1 a) A mixture of 2-chloropropanenitrile (0.2 mol) and 1,3-dichloro-5-nitrobenzene (0.2 mol) in DMSO (50 ml) was added dropwise at RT to a solution of NaOH (1 mol) in DMSO (150 ml) while the temperature was kept below 30° C. The mixture was stirred at RT for 1 hour, then poured out on ice and acidified with HCl. The precipitate was filtered off, washed with $H_2O$ and taken up in $CH_2Cl_2$. The organic solution was washed with $H_2O$, dried, filtered and the solvent was evaporated. The residue was purified by column chromatography over silica gel (eluent: $CH_2Cl_2$/cyclohexane 70/30). The pure fractions were collected and the solvent was evaporated, yielding 19.5 g (40%) of (±)-2,6-dichloro-α-methyl-4-nitrobenzeneacetonitrile (interm. 1).

b) NaH 80% (0.0918 mol) was added portionwise at 0° C. under $N_2$ flow to a solution of intermediate (1) (0.0612 mol) in DMF (100 ml). The mixture was stirred at 0° C. under $N_2$ flow for 1 hour. $CH_3I$ (0.0918 mol) was added dropwise at 0° C. The mixture was stirred at 50° C. for 12 hours, then poured out on ice and extracted with EtOAc. The organic layer was separated, washed with $H_2O$ dried, filtered and the solvent was evaporated, yielding 17.1 g of 2,6-dichloro-α,α-dimethyl-4-nitrobenzeneacetonitrile (interm. 2).

c) A mixture of intermediate (2) (0.066 mol) in $CH_3OH$ (200 ml) was hydrogenated at RT under a 3 bar pressure for 1 hour with Raney Nickel (15 g) as a catalyst. After uptake of $H_2$, the catalyst was filtered through celite, washed with $CH_3OH$ and the filtrate was evaporated, yielding 17.1 g of 4-amino-2,6-dichloro-cc,a-dimethylbenzene-acetonitrile (interm. 3).

d) Acetic acid anhydride (0.1484 mol) was added dropwise at RT to a solution of 4-amino-2,6-dichloro-a,a-dimethylbenzeneacetonitrile (0.0742 mol) in toluene (200 ml). The mixture was stirred and refluxed for 4 hours. The solvent was evaporated and the residue was taken up in $CH_2Cl_2$. The organic solution was washed with $K_2CO_3$ 10% and with $H_2O$, dried, filtered and the solvent was evaporated, yielding 19.0 g (95%) of N-[3,5-dichloro-4-(1-cyano-1-methylethyl)phenyl]acetonitrile (interm. 4).

e) A mixture of intermediate (4) (0.07 mol) and triethylamine (0.07 mol) in pyridine (150 ml) was stirred at 60° C. $H_2S$ was bubbled through the mixture. The mixture was stirred at 60° C. for 24 hours. $H_2S$ was bubbled through the mixture for another 24 hours. The solvent was evaporated and the residue was taken up in $CH_2Cl_2$ and $CH_3OH$. The organic solution was washed with HCl 3N and with $H_2O$, dried, filtered and the solvent was evaporated. The residue was crystallized from diethyl ether. The precipitate was filtered off and dried, yielding 14.7 g (69%) of N-[4-[1-(aminosulfinyl)-1-methylethyl]-3,5-dichlorophenyl]acetamide (interm. 5).

f) A mixture of intermediate (5) (0.0481 mol) and 2-bromo-1-phenylethanone (0.0529 mol) in ethanol (300 ml) was stirred and refluxed for 4 hours. The solvent was evaporated. The residue was taken up in $CH_2Cl_2$. The organic solution was washed with $H_2O$, dried, filtered and the solvent was evaporated, yielding 20.0 g of N-[3,5-dichloro-4-[1-methyl-1-(4-phenyl-2-thiazolyl)ethyl]phenyl]acetamide (interm. 6).

g) A mixture of intermediate (6) (0.0493 mol) in HCl 3N (200 ml) and ethanol (300 ml) was stirred at 60° C. for 12 hours. The solvent was evaporated. The residue was basified with a concentrated $NH_4OH$ solution and extracted with $CH_2Cl_2$. The organic layer was separated, washed with $H_2O$, dried, filtered and the solvent was evaporated. The residue was purified by column chromatography over silica gel (eluent: $CH_2Cl_2$/cyclohexane 70/30). The pure fractions were collected and the solvent was evaporated, yielding 6.5 g (36%) of 3,5-dichloro-4-[1-methyl-1-(4-phenyl-2-thiazolyl)-ethyl]benzeneamine (interm. 7).

h) A solution of $NaNO_2$ (0.017 mol) in a small amount of $H_2O$ was added at 5° C. to a solution of intermediate (7) (0.017 mol) in acetic acid (50 ml) and concentrated HCl (10 ml). The mixture was stirred at 0° C. for 35 minutes and then added to a solution of ethyl cyanoacetylcarbamate (0.0238 mol) and sodium acetate (62 g) in water (700 ml). The mixture was stirred at 0° C. for 45 minutes. The precipitate was filtered off, washed with $H_2O$ and centrifuged. The residue was taken up in EtOAc. The organic solution was washed with $H_2O$ dried, filtered and the solvent was evaporated, yielding 7.6 g (84%) of ethyl [[[3,5-dichloro-4-[1-methyl-1-(4-phenyl-2-thiazolyl)ethyl]phenyl]-hydrazono]cyanoacetyl]carbamate (interm. 8).

i) A mixture of intermediate (8) (0.0143 mol) and potassium acetate (0.015 mol) in acetic acid (70 ml) was stirred and refluxed for 3 hours and poured out into $H_2O$. The precipitate was filtered off and taken up in EtOAc. The organic solution was washed with $H_2O$ dried, filtered and the solvent was evaporated, yielding 8.3 g of 2-[3,5-dichloro-4-[1-methyl-1-(4-phenyl-2-thiazolyl)ethyl]phenyl]-2,3,4,5-tetrahydro-3,5-dioxo-1,2,4-triazine-6-carbonitrile (interm. 9).

j) A mixture of intermediate (9) (0.0171 mol) in concentrated HCl (25 ml) and acetic acid (75 ml) was stirred and refluxed for 3 hours. The mixture was cooled and poured out into $H_2O$. The precipitate was filtered off, washed with $H_2O$ and taken up in EtOAc. The organic solution was dried, filtered and the solvent was evaporated, yielding 6.8 g (79%) of 2-[3,5-dichloro-4-[1-methyl-1-(4-phenyl-2-thiazolyl)ethyl]-phenyl]-2,3,4,5-tetrahydro-3,5-dioxo-1,2,4-triazine-6-carboxylic acid (interm. 10).

EXAMPLE A2 a) A solution of $NaNO_2$ (0.36 mol) in $H_2O$ (50 ml) was added to a solution of intermediate (3) (0.34 mol) in acetic acid (700 ml) and HCl (102 ml), stirred at 10° C. The reaction mixture was stirred for 80 minutes at 10° C. A powdered mixture of sodium acetate (1.02 mol) and diethyl (1,3-dioxo-1,3-propanediyl)biscarbamate (0.374 mol) was added and the reaction mixture was stirred for 40 minutes. The reaction mixture was poured out onto crushed ice. The precipitate was filtered off, washed with water, taken up into $CH_2Cl_2$, and the layers were separated. The organic layer was dried, filtered and the solvent evaporated, yielding 138.5 g (84%) of diethyl N,N'-[2-[[3,5-dichloro-4-(1-cyano-1-methylethyl)phenyl]hydrazono]-1,3-dioxo-1,3-propanediyl]dicarbamate (interm. 11).

b) A solution of intermediate (11) (0.28 mol) and potassium acetate (0.28 mol) in acetic acid (1000 ml) was stirred and refluxed for 3 hours. The reaction mixture containing ethyl [[2-[3,5-dichloro-4-(1-cyano-1-methylethyl)phenyl]-2,3,4,5-tetrahydro-3,5-dioxo-1,2,4-triazin-6-yl]carbonyl]carbamate (interm. 12) was used as such in the next step.

c) Intermediate (12) (crude reaction mixture) was treated with HCl 36% (0.84 mol). The reaction mixture was stirred and refluxed for 4 hours, then stirred at RT over the weekend. The reaction mixture was poured out onto crushed ice and this mixture was extracted with $CH_2Cl_2$. The separated organic layer was dried, filtered and the solvent evaporated, yielding 111.6 g of 2-[3,5-dichloro-4-(1-cyano-1-methylethyl)phenyl]-2,3,4,5-tetrahydro-3,5-dioxo-1,2,4-triazine-6-carboxylic acid (interm. 13).

d) A suspension of intermediate (13) (0.28 mol) in mercaptoacetic acid (250.0 ml) was stirred for 4 hours at 100° C., then allowed to cool to RT and stirred overnight. The reaction mixture was poured out onto crushed ice and this mixture was extracted with $CH_2Cl_2$. The separated organic layer was dried, filtered and the solvent evaporated. Toluene was added and azeotroped on the rotary evaporator. The residue was purified by short column chromatography over silica gel (eluent: $CH_2Cl_2/CH_3OH$ 98/2). The pure fractions were collected and the solvent was evaporated. The residue was stirred in DIPE, filtered off, washed with DIPE, then dried, yielding 36.8 g (41%) of 2,6-dichloro-4-(4,5-dihydro-3,5-dioxo-1,2,4-triazin-2(3H)-yl)-α,α-dimethylbenzeneacetonitrile. The filtrate was stirred in DIPE and the resulting precipitate was filtered off, washed with DIPE, and dried, yielding 2.5 g (3%) of 2,6-dichloro-4-(4,5-dihydro-3,5-dioxo-1,2,4-triazin-2(3H)-yl)-α,α-dimethylbenzeneacetonitrile (interm. 14).

e) A solution of intermediate (14) (0.107 mol) and N,N-bis(1-methylethyl)ethanamine (0.315 mol) in pyridine (500 ml) was stirred and heated to 80° C. $H_2S$ was allowed to bubble through this solution for 24 hours at 80° C. $H_2S$ gas inlet was stopped and the reaction mixture was stirred over the weekend at RT. The solvent was evaporated. $CH_2Cl_2/CH_3OH$ (500 ml; 9:1) was added, and this mixture was poured out into 2 N HCl (1000 ml) at 0° C. The mixture was stirred for 10 minutes. The precipitate was filtered off and dried, yielding 23.2 g (64%) of 2,6-dichloro-4-(4,5-dihydro-3,5-dioxo-1,2,4]-α,α-dimethylbenzeneethanethioamide (interm. 15).

EXAMPLE A3 a) A solution of intermediate (3) (0.1484 mol) and triethylamine (0.15 mol) in pyridine (300 ml) was stirred at 60° C. $H_2S$ was allowed to bubble through the mixture for 4 days. More triethylamine (20 ml) was added and the reaction mixture was stirred for 24 hours. More triethylamine (10 ml) was added and $H_2S$ was bubbled through the mixture at 60° C. The solvent was evaporated. The residue was taken up into $CH_2Cl_2$ with a small amount of $CH_3OH$. The organic solution was washed with 3 N HCl and precipitation resulted. The precipitate was filtered off and was taken up into $CH_2Cl_2/CH_3OH$ (9:1), washed with $NaHCO_3$, with water, dried, filtered and the solvent was evaporated. The residue was boiled in diethyl ether, filtered off and dried, yielding 14.1 g (37%) of 4-amino-2,6-dichloro-α,α-dimethylbenzeneethanethioamide (interm. 16).

b) A mixture of intermediate (16) (0.04271 mol) and 3-amino-2-bromo-1-phenyl-propanone (0.043 mol) in ethanol (150 ml) was stirred for 4 hours at 50° C. under $N_2$ atmosphere. The solvent was evaporated and a 10% aqueous $K_2CO_3$ solution was added and this mixture was extracted with $CH_2Cl_2$. The separated organic layer was dried, filtered and the solvent evaporated. The residue was purified by column chromatography over silica gel (eluent: $CH_2Cl_2/CH_3OH$ from 100/0 to 97/3). The pure fractions were collected and the solvent was evaporated. The residue was dissolved in 2-propanol and converted into the hydrochloric acid salt (1:1) with 6 N HCl/2-propanol. The solvent was evaporated. The residue was recrystallized from 2-propanol. The precipitate was filtered off and dried, yielding 6.7 g (35%) of 2-[1-(4-amino-2,6-dichlorophenyl)-1-methylethyl-N,N-dimethyl-4-phenyl-5-thiazole-methanamine (interm. 17).

c) At 10° C., intermediate (17) (0.0141 mol) was stirred in a mixture of acetic acid (50 ml) and HCl, 37% (4.23 ml). A solution of $NaNO_2$ (0.01414 mol) in water (5 ml) was added dropwise over 15 minutes at 10° C. The reaction mixture was stirred for 1 hour at 10° C. Sodium acetate (0.0475 mol) and diethyl(1,3-dioxo-1,3-propanediyl)-biscarbamate (0.016 mol) were added in one portion and the resulting reaction mixture was stirred for one hour at RT. The reaction mixture was poured into ice-water (400 ml). $CH_2Cl_2$ (400 ml) was added and the aqueous layer was alklized with solid $NaHCO_3$. The separated organic layer was dried, filtered and the solvent evaporated, yielding 10.0 g of diethyl N,N'-[2-[[3,5-dichloro-4-[1-[5-[(dimethylamino)methyl-4-phenyl-2-thiazolyl]-1-methylethyl]phenyl]hydrazono]-1,3-dioxo-1,3-propanediyl]-dicarbamate (interm. 18).

d) Intermediate (18) (0.0148 mol) was dissolved in acetic acid (75 ml) at RT. Potassium acetate (0.0148 mol) was added and the resulting reaction mixture was stirred and refluxed for 3 hours. The solvent was evaporated, yielding ethyl [[2-[3,5-dichloro-4-[1-[5-[(dimethylamino)methyl]4-phenyl-2-thiazolyl]-1-methylethyl]-phenyl]-2,3,4,5-tetrahydro-3,5-dioxo-1,2,4-triazin-6-yl]carbonyl]carbamate (interm. 19).

e) A solution of intermediate (19) (0.0148 mol) in acetic acid (75 ml) and concentrated HCl (30 ml) was stirred and refluxed overnight. The solvent was evaporated, yielding 2-(3,5-dichloro-4-[1-[5-[(dimethylamino)methyl]-4-phenyl-2-thiazolyl]-1-methylethyl]-phenyl]-2,3,4,5-tetrahydro-3,5-dioxo-1,2,4-triazine-6-carboxylic acid (interm. 20).

EXAMPLE A4 a) $NaOCH_3$ 30% (0.592 mol) was added to a solution of hydroxylamine hydrochloride (0.1085 mol) in $CH_3OH$ (200 ml), stirred at RT. The mixture was stirred for 10 minutes. Intermediate (3) (0.0542 mol) was added portionwise and the resulting reaction mixture was stirred and refluxed overnight. The solvent was evaporated. The residue was partitioned between $CH_2Cl_2$ and water. The organic layer was separated, dried, filtered and the solvent was evaporated. The residue was stirred in DIPE, filtered off, washed with DIPE, and dried, yielding 3.7 g of (26%) 4-amino-2,6-dichloro-N'-hydroxy-α,α-dimethylbenzeneethanimidamide (interm. 21).

b) A solution of intermediate (21) (0.0323 mol) and N,N-bis(methylethyl)ethanamine (0.0339 mol) in $CH_2Cl_2$ (190 ml) was stirred at 15° C. A solution of 2-chlorobenzoyl chloride (0.0323 mol) in $CH_2Cl_2$ (10 Ml) was added dropwise and the resulting reaction mixture was stirred for one hour. Water was added. The organic layer was separated, dried, filtered and the solvent was evaporated. Toluene was added and azeotroped on the rotary evaporator, yielding 13.0 g of [1-amino-2-(4-amino-2,6-dichlorophenyl)-2-methylpropylidenyl]amino 2-chlorobenzoate (interm. 22).

c) A solution of intermediate (22) (0.0323 mol) and p-toluenesulfonic acid (0.0323 mol) in DMSO (100 ml) was stirred for 30 minutes at 150° C. The reaction mixture was cooled. Water was added and this mixture was extracted with toluene. The separated organic layer was dried, filtered and the solvent evaporated. The residue was purified by short column chromatography over silica gel (eluent: $CH_2Cl_2$). The desired fractions were collected and the solvent was evaporated. The concentrate was co-evaporated with EtOAc, yielding 11.7 g of 3,5-dichloro-4-[1-[5-(2-chlorophenyl)-1,2,4-oxadiazol-3-yl]-1-methylethyl]benzenamine (interm. 23).

d) A solution of intermediate (23) (0.0302 mol) and HCl conc. (0.0906 mol) in acetic acid (100 ml) was stirred at 0° C. A solution of $NaNO_2$ (0.032 mol) in water (10 ml) was added dropwise at 0° C. The reaction mixture was stirred for 1 hour at 0° C. A powdered mixture of sodium acetate (0.0906 mol) and diethyl(1,3-dioxo-1,3-propanediyl)biscarbamate (0.0332 mol) was added portionwise. The mixture was allowed to warm to RT and stirred for 1 hour. Water was added and this mixture was extracted with $CH_2Cl_2$. The separated organic layer was dried, filtered and the solvent evaporated, yielding diethyl N,N'-[2-[[3,5-dichloro-4-[1-[5-(2-chlorophenyl)-1,2,4-oxadiazol-3-yl]-1-methylethyl]phenyl]hydrazono]-1,3-dioxo-1,3-propanediyl]-dicarbamate (interm. 24).

e) A solution of intermediate (24) (0.0302 mol) and sodium acetate (0.0302 mol) in acetic acid (200 ml) was stirred and refluxed for 3 hours. The reaction mixture was poured out into water and this mixture was extracted with $CH_2Cl_2$. The separated organic layer was dried, filtered and the solvent evaporated. Toluene was added and azeotroped on the rotary evaporator, yielding ethyl [[2-[3,5-dichloro-4-[1-[5-(2-chloro-phenyl)-1,2,4-oxadiazol-3-yl]-1-methylethyl]phenyl]-2,3,4,5-tetrahydro-3,5-dioxo-1,2,4-triazin-6-yl]carbonyl]carbamate (interm. 25).

f) A mixture of intermediate (25) (0.0302 mol) in HCl 36% (10 ml) and acetic acid (200 ml) was stirred and refluxed overnight. The reaction mixture was poured out onto crushed ice and this mixture was extracted with $CH_2Cl_2$. The separated organic layer was dried, filtered and the solvent evaporated, yielding 16.3 g of 2-[3,5-dichloro-4-[1[5-[2-chlorophenyl)-1,2,4-oxidiazol-3-yl]-1-methyl]phenyl]-2,3,4,5-tetrahydro-3,5-dioxo-1,2,4-triazine-6-carboxylic acid (interm. 26).

The following intermediates were prepared analogous to the reaction procedure described in example A.4.

TABLE 1

| Int. No. | $R^{11}$ |
|---|---|
| 27 | phenyl |
| 28 | 3-fluoro-phenyl |
| 29 | 3-chloro-phenyl |
| 30 | 3-methyl-phenyl |
| 31 | 3-thienyl |
| 32 | 2-fluoro-phenyl |
| 33 | 2-methyl-phenyl |
| 34 | 4-fluoro-phenyl |
| 35 | 4-pyridinyl |

EXAMPLE A5

$SOCl_2$ (10 ml) was added to a solution of compound (19) (0.00669 mol) in $CH_2Cl_2$ (30 ml). The reaction solution was stirred and refluxed for 1 hour, then cooled and the solvent was evaporated. Toluene was added and azeotroped on the rotary evaporator, yielding 2-[1-[2,6-dichloro-4-(4,5-dihydro-3,5-dioxo-1,2,4-triazin-2(3H)-yl)phenyl]-1-methylethyl]-4-phenyl-5-thiazoleacetyl chloride (interm. 36).

EXAMPLE A6 a) A mixture of compound (56) (0.0163 mol) in $SOCl_2$ (50 mol) and $CH_2Cl_2$ (50 ml) was stirred at RT for about 3 hours. The solvent was evaporated and the residue was co-evaporated with toluene, yeilding 11.3 g of 3-[2-[1-[2,6-dichloro-4-(4,5-dihydro-3,5-dioxo-1,2,4-triazin-2(3H)-yl)phenyl]-1-methylethyl]-4-2-chlorophenyl)-5-thiazolyl]benzoyl chloride (interm. 37).

b) Reaction under $N_2$ atmosphere. 2-Methoxyethanamine (0.0020 mol) was added to a solution of compound (67) (0.001667 mol) in $CH_2Cl_2$ (25 ml) with $MgSO_4$ (0.800 g), stirred at RT. The reaction mixture was stirred for 3 days at RT. More 2-methoxy-ethanamine (2 equiv) was added and the reaction mixture was stirred overnight. $MgSO_4$ was removed by filtration and the filtrate containing 2-[3,5-dichloro-4-[1-[4-(2-chloro-phenyl)-5-[3-[[(2-methoxyethyl)imino]methyl]phenyl]-2-thiazolyl]-1-methylethyl]-phenyl]-1,2,4-triazine-3,5(2H,4H)-dione (interm. 38) was used as such in the subsequent reaction step.

EXAMPLE A7 a) A mixture of intermediate (14) (0.0308 mol) in acetic acid (120 ml) and $H_2SO_4$ (80 ml) was heated to 110° C. and stirred for 1.5 hours. The reaction mixture was allowed to cool to RT and poured out onto crushed ice. The precipitate was filtered off, washed, dissolved in $CH_2Cl_2/CH_3OH$ 90/10, dried, filtered and the solvent was evaporated. The residue was co-evaporated with toluene, yielding 9.1 g (86%) of 2,6-dichloro-4-(4,5-dihydro-3,5-dioxo-1,2,4-triazin-2(3H)-yl]-α,α-dimethylbenzene-acetamide (interm. 39).

b) A mixture of intermediate (39) (0.026 mol) in acetonitrile (180 ml) and water (180 ml) was stirred at RT, (diacetoxyiodo)benzene (0.029 mol) was added and the reaction mixture was stirred for 4 hours. The mixture was poured out into ice-water (400 ml). HCl (20 ml) was added dropwise. The reaction mixture was stirred for 30 minutes and washed with DIPE. The aqueous layer was basified with NaOH 50% and the solvent was evaporated. The residue was extracted with EtOAc and then with $CH_3OH/CH_2Cl_2$ 90/10. The combined organic layers were dried, filtered and the solvent was evaporated. The residue was co-evaporated with toluene and dried, yielding 6.2 g (75%) of 2-[4-(1-amino-1-methylethyl)-3,5-dichlorophenyl]-1,2,4-triazine-3,5(2H,4H)-dione (interm. 40).

c) A mixture of intermediate (40) (0.0032 mol) in tetrahydrofuran (5 ml) was stirred at RT. A solution of benzoyl isothiocyanate (0.0035 mol) in THF (25 ml) was added dropwise at RT and the reaction mixture was stirred for 3 hours. The solvent was removed and the residue was dissolved in $CH_2Cl_2$ and washed with $H_2O$. The separated organic layer was dried, filtered and the solvent was evaporated, yielding 1.5 g of N-benzoyl-N'-[1-[2,6-dichloro-4-(4,5-dihydro-3,5-dioxo-1,2,4-triazin-2(3H)-yl)-phenyl]-1-methylethyl]thiourea (interm. 41).

EXAMPLE A8

A mixture of compound (50) (0.0018 mol) in toluene (40 ml) was stirred and heated to 60° C. The mixture was treated with HCl gas for 3 hours and heated to reflux temperature. Then, the mixture was treated with phosgene gas for 4 hours. N₂ gas was bubbled through the reaction mixture for 1 hour. The solvent was evaporated, yielding 2-[3,5-dichloro-4-[1-methyl-1-[5-(3-nitrosophenyl)-4-phenyl-2-thiazolyl]ethyl]phenyl]-1,2,4-triazine-3,5(2H,4H)-dione (interm. 42).

EXAMPLE A9 a) A mixture of (±)-α-(4-amino-2,6-dichlorophenyl)-2-pyridineacetonitrile (0.324 mol) in H₂SO₄ 90% (900 ml) was stirred at 90° C. for 2 hours, then poured out on ice and basified with a concentrated NH₄OH solution. The precipitate was filtered off, washed with H₂O and centrifuged. The residue was dried, yielding 86.0 g (90%) of (±)-α-(4-amino-2,6-dichlorophenyl)-2-pyridineacetamide (interm. 43).

b) Starting from intermediate 43 and using the same reaction procedures as described in example A2a) through A2c), (±)-2-[4-[2-amino-2-oxo-(2-pyridinyl)ethyl]-3,5-dichloro-phenyl]-2,3,4,5-tetrahydro-3,5-dioxo-1,2,4-triazine-6-carboxylic acid (interm. 44) was prepared.

EXAMPLE A10 a) A mixture of (±)-2,6-dichloro-α-methyl-4-nitrobenzeneacetonitrile (0.1632 mol) in a mixture of H₂SO₄/H₂O/acetic acid (150 ml) was stirred and refluxed for 2 hours, then poured out onto crushed ice and this mixture was extracted with CH₂Cl₂. The separated organic layer was dried, filtered and the solvent evaporated. The residue was purified by short column chromatography over silica gel (eluent: CH₂Cl₂/CH₃OH 98/2). The desired fractions were collected and the solvent was evaporated, yielding 31.9 g (74%) of (±)-2,6-dichloro-α-methyl-4-nitrobenzeneacetic acid (interm. 45).

b) A solution of intermediate (45) (0.0756 mol) in SOCl₂ (200 ml) was stirred and refluxed for 2 hours. The solvent was evaporated. Toluene was added and azeotroped on the rotary evaporator, yielding (±)-2,6-dichloro-α-methyl-4-nitrobenzeneacetyl chloride (interm. 46).

c) A solution of intermediate (46) (0.0756 mol) in CH₂Cl₂ (50 ml) was added to a solution of benzoylhydrazine (0.0756 mol) and N,N-(1-methylethyl)ethaneamine (0.0832 mol) in CH₂Cl₂ (250 ml), stirred at 0° C. The reaction mixture was stirred for one hour at RT. Water was added. The organic layer was separated, dried, filtered and the solvent was evaporated. The residue was purified by short column chromatography over silica gel (eluent: CH₂Cl₂/CH₃OH 97/3). The desired fractions were collected and the solvent was evaporated. The residue was stirred in diethyl ether, filtered off, washed with diethyl ether and dried, yielding 27.5 g (95%) of (±)-2,6-dichloro-α-methyl-4-nitrobenzeneacetic acid (benzoyl)hydrazide (interm. 47).

d) A mixture of intermediate (47) (0.072 mol) in POCl₃ (250 ml) was stirred overnight at RT. The solvent was evaporated. Toluene was added and azeotroped on the rotary evaporator. The residue was taken up into CH₂Cl₂, washed with a 10% aqueous NaHCO₃ solution, dried, filtered and the solvent was evaporated. The residue was crystallized from diethyl ether, filtered off, washed with diethyl ether and dried in vacuo, yielding 20.1 g (77%) of (±)-2-[1-(2,6-dichloro-4-nitrophenyl)ethyl]-5-phenyl-1,3,4-oxodiazole (interm. 48).

e) A mixture of intermediate (48) (0.023 mol) in CH₃OH (150 ml) was hydrogenated with palladium on activated charcoal (5%) (2 g) as a catalyst in the presence of thiophene (2 ml). After uptake of hydrogen (3 equiv), the catalyst was filtered off over dicalite and the filtrate was evaporated. The residue was crystallized from diethyl ether, filtered off, washed with diethyl ether and dried, yielding 5 g (65%) of (±)-3,5-dichloro-4-[1-(5-phenyl-1,3,4-oxodiazol-2-yl)ethyl]benzeneamine (interm. 49).

B. Preparation of the Final Compounds

EXAMPLE B1 a) A mixture of intermediate (10) (0.0133 mol) in mercaptoacetic acid (7 ml) was stirred at 175° C. for 2 hours. The mixture was cooled, poured out into ice water, basified with K₂CO₃ and extracted with EtOAc. The organic layer was separated, washed with H₂O dried, filtered and the solvent was evaporated. The residue was purified by column chromatography over silica gel (eluent: CH₂Cl₂/CH₃OH 99/1). The pure fractions were collected and the solvent was evaporated, yielding 2.2 g (36%) of 2-[3,5-dichloro-4-[1-methyl-1-(4-phenyl-2-thiazolyl)ethyl]phenyl]-1,2,4-triazine-3,5(2H,4H)-dione (comp. 1).

b) A mixture of intermediate (44) (0.00958 mol) in mercaptoacetic acid (30 ml) was stirred at 175° C. for 3 hours and then allowed to cool to RT. CH₂Cl₂ and ice was added. Then K₂CO₃ 10% was added. The organic layer was separated, dried, filtered and the solvent was evaporated. The residue was purified by column chromatography over silica gel (eluent: CH₂Cl₂/CH₃OH 97/3). The pure fractions were collected and the solvent was evaporated. The residue was taken up in K₂CO₃ 10%. The mixture was washed with CH₂Cl₂ and acidified with HCl 6N. The precipitate was filtered off, washed with 2-propanone and dried, yielding 0.4 g of 2-[3,5-dichloro-4-(2-pyridinyl-methyl)phenyl]-1,2,4-triazine-3,5(2H,4H)-dione hydrochloride(:1); hydrate(1:1) (comp. 107).

EXAMPLE B2

A solution of intermediate (15) (0.0111 mol) and 2-bromo-1-(3-chlorophenyl)-1-propanone (0.0121 mol) in ethanol (40 ml) and DMF (40 ml) was stirred for 4 hours at 80° C. The solvent was evaporated. Toluene was added and azeotroped on the rotary evaporator. The crude oil was stirred in CH₂Cl₂, washed with water, dried, filtered and the solvent was evaporated. The residue was crystallized from EtOAc. The precipitate was filtered off, washed with EtOAc, and dried, yielding 4.3 g (76%) of 2-[3,5-di-chloro-4-[1-[4-(3-chlorophenyl)-5-methyl-2-thiazolyl]-1-methylethyl]phenyl]-1,2,4-triazine-3,5(2H,4H)-dione (comp. 3).

EXAMPLE B3 a) A mixture of compound (9) (0.00183 mol) and NaOH 1N (0.0055 mol) in CH₃OH (25 ml) and THF (25 ml) was stirred overnight at RT. The reaction mixture was acidified with 1N HCl (8 ml), and the product was taken up into EtOAc. The organic layer was washed with brine, dried, filtered and the solvent was evaporated. The residue was crystallized from CH₃CN. The precipitate was filtered off, washed with DIPE, and dried, yielding 0.8 g (79%) of 2-[1-[2,6-dichloro-4-(4,5-dihydro-3,5-dioxo-1,2,4-triazin-2 (3H)-yl)phenyl]1-α-methylethyl]-4-phenyl-5-thiazoleacetic acid (comp. 19).

b) A mixture of compound (19) (0.00483 mol), 1,4'-bipiperidine dihydrochloride (0.0058 mol) and N-ethyl-N-(1-methylethyl)-2-propanamine (0.0145 mol) in CH₂Cl₂ (50 ml) was stirred and cooled to 0° C. under N₂ atmosphere. N'-(ethylcarbonimidoyl)-N,N-dimethyl-1,3-propanediamine monohydrochloride (0.0058 mol) was added at 0° C. The mixture was allowed to warm to RT, then stirred overnight. Water was added and this mixture was extracted with $CH_2Cl_2/CH_3OH$ (9:1). The separated organic layer was dried, filtered and the solvent evaporated. The residue was purified by column chromatography over silica gel (eluent: $CH_2Cl_2/CH_3OH$ 92.5/7.5). The desired fractions were collected and the solvent was evaporated. The residue was further purified by HPLC over silica gel (eluent: $CH_2Cl_2/CH_3OH$ gradient from 100/0 to 90/10 in 30 min). The desired fractions were collected and the solvent was evaporated. The residue was stirred in boiling DIPE, then filtered off and dried, yielding 1.0 g (33%) of 1'-[[2-[1-[2,6-dichloro-4-(4,5-dihydro-3,5-dioxo-1,2,4-triazin-2(3H)-yl)phenyl]-1-methylethyl-4-phenyl-5-thiazolyl]acetyl]-(1,4'-dipiperidine) (comp. 24).

EXAMPLE B4

A solution of intermediate (36) (0.00334 mol) in $CH_2Cl_2$ (20 ml) was stirred at RT. N,N-bis(1-methylethyl)ethanamine (0.00668 mol) was added. A solution of 1-(phenylmethyl)piperazine (0.0067 mol) in $CH_2Cl_2$ (10 ml) was added slowly at 0° C. The reaction mixture was stirred overnight at RT. $CH_2Cl_2$ was added. Brine was added. The organic layer was separated, dried, filtered and the solvent was evaporated. The residue was purified by HPLC over silica gel (eluent: $CH_2Cl_2/CH_3OH$ from 100/0 to 90/10 in 30 minutes). The pure fractions were collected and the solvent was evaporated. The residue was stirred in DIPE, filtered off and dried, yielding 0.3 g (15%) of 1-[[2-[1-[2,6-dichloro-4-(4,5-dihydro-3,5-dioxo-1,2,4-triazin-2(3H)-yl)-phenyl]-1-methylethyl]-4-phenyl-2-thiazolyl]acetyl-4-phenylmethyl)piperazine (comp. 35).

EXAMPLE B5

Sodium (0.0067 mol) was dissolved in ethanol (8 ml) at 0° C. under $N_2$ flow and then added dropwise at RT under $N_2$ flow to a stirring solution of compound (25) (0.0067 mol) in THF (40 ml). The mixture was heated to reflux temperature. $NaBH_4$ (0.010 mol) was added portionwise. The mixture was stirred for 30 minutes, then cooled to RT, poured out into ice water, acidified with a concentrated HCl solution and extracted with $CH_2Cl_2$. The organic layer was separated, washed with $H_2O$ dried, filtered and the solvent was evaporated. The residue was crystallized from ethanol. The precipitate was filtered off, washed with DIPE and dried, yielding 3.7 g (99%) of (±)-2-[3,5-dichloro-4-[1-[5-(hydroxyphenylmethyl)4-phenyl-2-thiazolyl]-1-methylethyl]phenyl]-1,2,4-triazin-3,5(2H,4H)-dione (comp. 29).

EXAMPLE B6 a) A solution of compound (30) (0.00457 mol) in $CH_2Cl_2$ (60 ml) was stirred at RT. $BBr_3$ 1M in $CH_2Cl_2$ (0.0137 mol) was added dropwise. The mixture was stirred and refluxed for 16 hours, then treated with $CH_3OH$ (15 ml) and washed with $H_2O$. The organic layer was separated, dried, filtered and the solvent was evaporated, yielding 2.1 g of (84%) 2-[4-[1-[5-(bromomethyl)4-phenyl-2-thiazolyl]-1-methylethyl]-3,5-dichlorophenyl]-1,2,4-triazine-3,5(2H,4H)-dione (comp. 41).

b) A mixture of compound (41) (0.0018 mol), 1-(methoxyethyl)piperazine (0.0018 mol) and $K_2CO_3$ (0.0036 mol) in $CH_3CN$ (50 ml) was stirred and refluxed for 16 hours. The solvent was evaporated and the residue was dissolved in $CH_2Cl_2$ and washed with $H_2O$. The organic layer was dried, filtered and the solvent was evaporated. The residue was purified by flash chromatography over silica gel (eluent: $CH_2Cl_2/CH_3OH$ 99.8/0.2, 99/1 and 95/5). The desired fractions were collected and the solvent was evaporated. The residue was stirred in DIPE. The precipitate was filtered off, washed and dried, yielding 0.6 g (55%) of 2-[3,5-dichloro-4-[1-[5-[[4-(2-methoxyethyl)-1-piperazinyl]methyl]-4-phenyl-2-thiazolyl]-1-methylethyl]phenyl]-1,2,4-triazine-3,5(2H,4H)-dione (comp. 42).

EXAMPLE B7 a) A mixture of compound (49) (0.036 mol) in THF (300 ml) was hydrogenated at 50° C. with Pt/C 5% (3 g) as a catalyst in the presence of thiophene (3 ml). After partial uptake of $H_2$, the catalyst was filtered off and the filtrate was concentrated. The residual fraction was hydrogenated again with Pt/C 5% (5 g) as a catalyst. After uptake of $H_2$, the catalyst was filtered off and the filtrate was evaporated. The residue was purified by HPLC over silica gel (eluent: $CH_2Cl_2/CH_3OH$ 98/2). The desired fractions were collected and their solvent was evaporated. The residue was stirred in DIPE. filtered off, washed and dried, yielding 11 g of 2-[4-[1-[5-(3-aminophenyl)4-phenyl-2-thiazolyl]-1-methylethyl]-3,5-dichlorophenyl]-1,2,4-triazine-3,5(2H,4H)-dione (comp. 50).

b) A mixture of compound (50) (0.0018 mol), acetic acid anhydride (0.0024 mol) and N,N-dimethyl-4-pyridinamine (0.0021 mol) in $CH_2Cl_2$ (15 ml) was stirred for 30 minutes at RT. More $CH_2Cl_2$ was added and the resulting solution was washed with a 5% aqueous $NaHCO_3$ solution, with 1N HCl and with water, dried, filtered and the solvent was evaporated. The residue was purified by flash column chromatography over silica gel (eluent: $CH_2Cl_2/CH_3OH$ 99.8/0.2 up to 98/2). The desired fractions were collected and the solvent was evaporated. The residue was stirred in DIPE, filtered off and dried, yielding 0.7 g (65%) of N-[3-[2-[1-[2,6-dichloro-4-(4,5-dihydro-3,5-dioxo-1,2,4-triazin-2(3H)-yl)phenyl]-1-methylethyl]4-phenyl-5-thiazolyl]phenyl]-acetamide (comp. 51).

c) A mixture of compound (50) (0.0018 mol) and cyanic acid sodium salt (0.0117 mol) in acetic acid (30 ml) and water (60 ml) was stirred for two days at 40° C. The solvent was evaporated. The residue was taken up into water. This mixture was extracted with $CH_2Cl_2/CH_3OH$ (90/10). The organic layer was separated, dried, filtered and the solvent was evaporated. The residue was dissolved in acetic acid (50 ml) and $H_2O$ (5 ml). The resulting suspension was stirred for 2 hours at 60° C. The solution was allowed to cool to RT, then concentrated. The residue was taken up into water, then extracted with $CH_2Cl_2/CH_3OH$ (90/10). The separated organic layer was dried, filtered and the solvent evaporated. The residue was purified by HPLC over silica gel (eluent: $CH_2Cl_2/CH_3OH$ 100/0, 90/10 (30 minutes)). The pure fractions were collected and the solvent was evaporated. The residue was stirred in DIPE, filtered off, washed and dried, yielding 0.5 g of N-[3-[2-[1-[2,6-dichloro-4-(4,5-dihydro-3,5-dioxo-1,2,4-triazin-2(3H)-yl)phenyl]-1-methylethyl]-4-phenyl-5-thiazolyl]phenyl]urea (comp. 54).

d) A solution of compound (50) (0.0009 mol) and N,N-bis(1-methylethyl)ethanamine (0.0013 mol) in $CH_2Cl_2$ (20 ml) was stirred and cooled to 0–5° C. A solution of sulfamoyl chloride (0.0013 mol) in $CH_2Cl_2$ (10 ml) was added dropwise at 0° C. The reaction mixture was stirred for another 2 hours and $H_2O$ (20 ml) was added. The separated organic layer was dried, filtered and the solvent was evaporated. The residue was purified by HPLC over Kromasil C18 (eluent: (0.5% ammonium acetate in $H_2O$)/$CH_3OH$/$CH_3CN$ 67.5/25/7.5; after 10 minutes 0/50/50). The pure fractions were collected and the solvent was evaporated. The residue was stirred in DIPE. The precipitate was filtered off, washed and dried, yielding 0.3 g of N-[3-[2-[1-[2,6-di-chloro-4-(4,5-dihydro-3,5-dioxo-1,2,4-triazin-2(3H)-yl)phenyl-1-methylethyl]4-phenyl-5-thiazolyl]phenyl]sulfamide (comp. 60).

e) A mixture of compound (50) (0.00227 mol) and D-glucose (0.750 g) in ethanol (50 ml) and DMF (25 ml) was stirred overnight at 100° C under $N_2$ atmosphere. More D-glucose (0.200 g) was added and the reaction mixture was stirred for 3 hours at 100° C. The solvent was evaporated. The residue was purified by HPLC (eluent: (0.5% ammonium acetate in $H_2O)/CH_3OH/CH_3CN 40/30/30$). The desired fractions were collected and the solvent was evaporated. $CH_3CN$ was added to the oil and precipitation resulted. The residues were repurified by column chromatography over silica gel (eluent: $CH_2Cl_2/CH_3OH$ from 90/10 to 0/100). The desired fractions were collected and the solvent was evaporated. The residue was stirred in DIPE, filtered off, dried, yielding 0.5 g (31%) of (α+β)-2-[3,5-dichloro-4-[1-[5-[3-[[tetrahydro-3,4,5-trihydroxy-6-hydroxymethyl)-2H-pyran-2H-pyran-2-yl]amino]phenyl]-4-phenyl-2-thiazolyl]-1-methylethyl]phenyl]-1,2,4-triazine-3,5(2H,4H)-dione 2-propanolate(1:1)(comp. 64).

EXAMPLE B8 a) A solution of compound (55) (0.0137 mol) in acetic acid (90 ml) was stirred at RT. HBr 48% (75 ml) was added and the reaction mixture was stirred overnight at 90° C., then for 7 days at 100° C. More HBr 48% (20 ml) was added and the resulting reaction mixture was poured out into water (600 ml). This mixture was extracted with $CH_2Cl_2/CH_3OH$ 95/5. The precipitate was filtered off from the organic and aqueous layer. The solid was stirred in boiling $CH_3CN$, then cooled to RT. The precipitate was filtered off and dried, washed with DIPE and dried. The product was stirred in $CH_2Cl_2/CH_3OH$ 90/10 (100 ml) and a saturated aqueous $NaHCO_3$ solution (50 ml), filtered off, washed with water, then with $CH_2Cl_2/CH_3OH$ 90/10, and dried, yielding 4.4 g of 2-[3,5-dichloro-4-[1-[5-(3-hydroxyphenyl)4-phenyl-2-thiazolyl]-1-methyl-ethyl]phenyl]-1,2,4-triazine-3,5(2H,4H)-dione (comp. 58).

b) A mixture of compound (58) (0.00363 mol) and N,N-bis(1-methylethyl)ethanamine (0.00718 mol) in $CH_2Cl_2$ (40 ml) was stirred at 0–5° C. under $N_2$ atmosphere. A mixture of sulfamoyl chloride (0.00508 mol) in $CH_2Cl_2$, (20 ml) was added in one portion. The resulting reaction mixture was stirred for 1 hour at 0° C., then stirred overnight at RT. More sulfamoyl chloride (0.3 g) was added and the reaction mixture was stirred for 2 hours at 40° C., then stirred further overnight. Water was added. $CH_2Cl_2/CH_3OH$ 95/5 was added and the layers were separated. The organic layer was separated, washed with water, dried, filtered and the solvent was evaporated. The residue was purified by HPLC over silica gel (eluent: $CH_2Cl_2/CH_3OH$ 100/0 to 97/3 over 30 minutes), then over RP-18 BDS (eluent: (0.5% ammonium acetate in $H_2O)/CH_3OH/CH_3CN$ 36/32/32, then 8/46/46 and finally 0/0/100). The desired fractions were collected and the solvent was evaporated, yielding 0.5 g of 3-[2-[1-[2,6-dichloro-4-(4,5-dihydro-3,5-dioxo-1,2,4-triazin-2(3H)-yl) phenyl]-1-methylethyl]-4-phenyl-5-thiazolyl] phenylsulfamate (ester) (comp. 66).

EXAMPLE B9 a) A solution of intermediate (37) (0.0163 mol) in 1,4-dioxane (125 ml) was stirred at RT under $N_2$ flow. $NaBH_4$ (0.0815 mol) was added portionwise. More $NaBH_4$ (0.0264 mol) was added portionwise and the reaction mixture was stirred at RT overnight. HCl 1N (80 ml) was added dropwise till a pH of about 4. The mixture was poured out into water (200 ml) and extracted with $CH_2Cl_2$. The organic layer was washed with water, dried, filtered and the solvent was evaporated. The residue was purified by flash column chromatography over silica gel (eluent: $CH_2Cl_2/CH_3OH$ 99/1, then 98/2 and finally 95/5). The desired fractions were collected and the solvent was evaporated. The residue was co-evaporated with EtOAc, then crystallized from $CH_3CN$. The precipitate was filtered off, washed with DIPE and dried, yielding 5.0 g of 2-[3,5-dichloro-4-[1-[4-(2-chlorophenyl)-5-[3-(hydroxymethyl)phenyl]-2-thiazolyl]-1-methylethyl]phenyl]-1,2,4-triazine-3,5(2H,4H)-dione (comp. 59).

b) $MnO_2$ (0.008335 mol) was added portionwise to a solution of compound (59) (0.001667 mol) in $CH_2Cl_2$ (15 ml). The mixture was stirred for 1 hour. More $MnO_2$ (0.008335 mol) was added and the reaction mixture was stirred again for 1 hour, then heated to 50° C. and stirred overnight at 50° C. The reaction mixture was cooled, filtered over dicalite and the filtrate was evaporated, yielding 3-[2-[1-[2,6-dichloro-4-(4,5-dihydro-3,5-dioxo-1,2,4-triazin-2 (3H)-yl)phenyl]-1-methylethyl]4-(2-chlorophenyl)-5-thiazolyl]benzaldehyde (comp. 67).

c) A mixture of intermediate (38) (0.000305 mol) and $NaB(OAc)_3H$ (0.000458 mol) in 1,2-dichloroethane (3.0 ml) was stirred at RT under $N_2$ atmosphere. Acetic acid (1.0 ml) was added dropwise and the reaction mixture was stirred over the weekend at RT, yielding 2-[3,5-dichloro-4-[1-[4-(2-chlorophenyl)-5-[3-[[(2-methoxyethyl)amino]-methyl] phenyl]-2-thiazolyl]-1-methylethyl]phenyl]-|1,2,4-triazine-3,5(2H,4H)-dione (comp. 68).

EXAMPLE B10

A solution of intermediate (37) (0.00407 mol) in $CH_2Cl_2$ (40 ml) was stirred at RT under $N_2$ atmosphere. A solution of 2-methoxyethanamine (0.0122 mol) in $CH_2Cl_2$ (15 ml) was added dropwise and the reaction mixture was stirred overnight at RT. Water (100 ml) was added. $CH_2Cl_2/CH_3OH$ 9515 (100 ml) was added and the biphasic mixture was acidified to a pH of about 5 with 1N HCl. The organic layer was separated, washed with water, dried, filtered and the solvent was evaporated, then co-evaporated with EtOAc. The residue was stirred in boiling 2-methoxy-2-methyl-propane, then cooled to RT, filtered off, washed and dried. This fraction was taken up into $CH_2Cl_2/CH_3OH$ 90/10, washed with half-saturated $NaHCO_3$ solution, with 1N HCl, with water, then dried, filtered and the solvent was evaporated, then co-evaporated with EtOAc. The residue was stirred in boiling 2-methoxy-2-methyl-propane, filtered off while still hot and the filtrate was evaporated. The residue was dried, yielding 0.7 g of 3-[2-[1-[2,6-dichloro-4-(4,5-dihydro-3,5-dioxo-1,2,4-triazin-2(3H)-yl)phenyl]-1-methylethyl-4-(2-chlorophenyl)-5-thiazolyl]-N-(2-methoxyethyl)-benzamide (comp. 63).

EXAMPLE B11

$NH_3$ 25% (40 ml) was stirred at 0° C. A solution of intermediate 37 (0.00407 mol) in 1,4-dioxane (20 ml) was added dropwise and the resulting reaction mixture was stirred overnight at RT. Concentrated HCl (35 ml) was added dropwise at 0° C. Water (100 ml) was added and this mixture was extracted with $CH_2Cl_2/CH_3OH$ 95/5 (150 ml). The separated organic layer was washed with water, dried, filtered and the solvent evaporated. EtOAc was added and azeotroped on the rotary evaporator. The residue was crystallized from 2-propanol. The precipitate was filtered off, washed with 2-propanol and DIPE, and dried, yielding 0.8 g (33%) of 3-[2-[1-[3,5-dichloro-4-(4,5-dihydro-3,5-dioxo-1,2,4-triazin-2(3H)-yl)phenyl]-1-methylethyl]-4-(2-chlorophenyl)-5-thiazolyl]benzamide (comp. 62).

EXAMPLE B12

A mixture of intermediate (41) (0.0025 mol) in H$_2$O (30 ml) was stirred at RT and NaOH 10% (15 ml) was added. The reaction mixture was stirred at 100° C. for 45 minutes and acidified at RT with 1N HCl. The precipitate was filtered off, washed with H$_2$O and dried, yielding 0.5 g of N-[1-[2,6-dichloro-4-(4,5-dihydro-3,5-dioxo-1,2,4-triazin-2(3H)-yl]phenyl]-1-methylethyl]thiourea (comp. 99).

EXAMPLE B13

A solution of 3-pyridinecarboxylic acid (0.003 mol) and triethyl amine (0.003 mol) in CH$_3$CN (30 ml) was stirred at RT. benzotriazol-1-yloxytris(dimethylamino) phosphonium hexafluorophosphate (0.003 mol) was added portionwise and the mixture was stirred for 45 minutes. Intermediate 40 (0.003 mol) was added and the resulting reaction mixture was stirred overnight. The solvent was evaporated. The residue was purified by flash column chromatography over silica gel (eluent: CH$_2$Cl$_2$/CH$_3$OH 99.5/0.5 up to 97.5/2.5). The desired fractions were collected and the solvent was evaporated. The residue was stirred in CH$_2$Cl$_2$, filtered off, washed and dried, yielding 0.4 g of N-[1-[2,6-dichloro-4-(4,5-dihydro-3,5-dioxo-1,2,4-triazin-2(3H)-yl)phenyl]-1-methylethyl]-3-pyridinecarboxamide (comp. 101).

EXAMPLE B14

A mixture of compound (56) (0.00407 mol) in CH$_2$Cl$_2$, p.a. (30 ml) was stirred at RT under N$_2$ flow. 1,1'-carbonylbis-1H-imidazole (0.00407 mol) was added portionwise and the reaction mixture was stirred at RT for 20 minutes. More 1,1'-carbonylbis-1H-imidazole (0.00086 mol) was added and the reaction mixture was stirred further at RT for 30 minutes. A solution of 1-methylpiperazine (0.0122 mol) in CH$_2$Cl$_2$ (10 ml) was added dropwise and the reaction mixture was stirred at RT for 1 hour. CH$_2$Cl$_2$/CH$_3$OH 80/20 (50 ml) was added. The organic layer was washed with a half-saturated NaCl solution, separated, dried, filtered, and the solvent was evaporated and then co-evaporated with EtOAc. The residue was purified by flash column chromatography over silica gel (eluent: CH$_2$Cl$_2$/CH$_3$OH 99.5/0.5, 97/3 and 90/101). The desired fractions were collected, and the solvent was evaporated and then co-evaporated with EtOAc. The residue was crystallized from 2-propanol. The precipitate was filtered off, washed with DIPE and dried, yielding 0.7 g (25%) of 1-[3-[2-[1-[2,6-dichloro-4-(4,5-dihydro-3,5-dioxo-1,2,4-triazin-2(3H)-yl)phenyl]-1-methylethyl]-4-(2-chlorophenyl)-5-thiazolyl]benzoyl]-4-methylpiperazine (comp. 61).

EXAMPLE B15 a) A solution of intermediate (42) (0.0009 mol) in THF (20 ml) was stirred at RT under N$_2$ atmosphere. A solution of 1-(phenylmethyl)piperazine (0.0009 mol) in TBF (5 ml) was added dropwise. The reaction mixture was stirred overnight at RT. The solvent was evaporated, yielding N-[3-[2-[1-[2,6-dichloro-4-(4,5-dihydro-3,5-dioxo-1,2,4-triazin-2(3H)-yl)phenyl]-1-methylethyl]-4-phenyl-5-thiazolyl]phenyl]4-(phenylmethyl)-1-piperazinecarboxamide (comp. 70).

b) 1-chloroethyl chloroformate (0.00117 mol) was added slowly to a solution of compound (70) (0.0009 mol) in CH$_2$Cl$_2$ (15 ml), stirred at 0° C. The reaction mixture was stirred for 90 minutes at 0° C. The solvent was evaporated and the residue was dissolved in methanol (30 ml). The mixture was stirred and refluxed for 1 hour. The solvent was evaporated. The residue was purified by flash column chromatography over silica gel (eluent: CH$_2$Cl$_2$/CH$_3$OH 97.5/2.5). The desired fractions were collected and the solvent was evaporated. The residue was further purified by HPLC over RP-18 (BDS; eluent: (0.5% ammonium acetate in H$_2$O)/CH$_3$OH/CH$_3$CN; gradient from 36/32/32 to 8/46/46 in 24 minutes and then to 0/0/100 in 32 minutes). The pure fractions were collected and the solvent was evaporated. The residue was stirred in DIPE, filtered off, washed and dried, yielding 0.1 g of N-[3-[2-[1-[2,6-dichloro-4-(4,5-dihydro-3,5-dioxo-1,2,4-triazin-2(3H)-yl)phenyl]-1-methylethyl]-4-phenyl-5-thiazolyl]-phenyl]-1-piperazinecarboxamide monohydrate (comp. 71).

EXAMPLE B16 a) A mixture of compound (87) (0.0011 mol), 1-bromo-2,5-pyrrolinedione (0.0011 mol) and dibenzoyl peroxide (catalytic quantity) in CCl$_4$ (30 ml) was stirred and refluxed for 3 hours. The mixture was allowed to cool to RT. The mixture was filtered over dicalite and the filtrate contained 2-[4-[1-[5-[2-(bromomethyl)phenyl]-1,2,4-oxadiazol-3-yl]-1-methylethyl]-3,5-dichlorophenyl]-1,2,4-triazine-3,5(2H,4H)-dione (comp 95).

b) A solution of compound (95) (0.0011 mol) in CCl$_4$ (30 ml) was stirred at RT. 1-Methylpiperazine (0.0033 mol) was added dropwise and the resulting reaction mixture was stirred and refluxed for 1 hour. The solvent was evaporated and the crude residue was filtered over dicalite (eluent: CH$_2$Cl$_2$/CH$_3$OH 97/3, 95/5 and 85/15). The desired fractions were collected and the solvent was evaporated. The residue was dissolved in 2-propanol and converted into the HCl salt (1:3) with HCl/2-propanol. The precipitate was filtered off, washed, and dried, yielding 0.3 g of 2-[3,5-dichloro-4-[1-methyl-1-[5-[2-[(4-methyl-1-piperazinyl) methyl]phenyl]-1,2,4-oxadiazol-3-yl]ethyl]phenyl]-1,2,4-triazine-3,5(2H,4H)-dione trihydrochloride (comp. 94).

EXAMPLE B17 a) A mixture of compound (74) (0.0049 mol) in CH$_3$OH (100 ml) and THF (30 ml) was hydrogenated at RT under a 3 bar pressure for 3 hours with Raney Nickel (2.5 g) as a catalyst. After uptake of H$_2$, the catalyst was filtered through celite, washed with CH$_3$OH and TBF and the filtrate was evaporated. The residue (1.5 g) was purified by column chromatography over silica gel (eluent: CH$_2$Cl$_2$/CH$_3$OH 97/3). The pure fractions were collected and the solvent was evaporated, yielding 1.3 g (53%) of 2-[4-[1-[4-(5-amino-2-thienyl)-2-thiazolyl]-1-methylethyl]-3,5-dichlorophenyl]-1,2,4-triazine-3,5(2H,4H)-dione (comp. 80).

b) Methanesulfonyl chloride (0.0044 mol) was added dropwise at 10° C. under N$_2$ flow to a solution of compound (80) (0.00208 mol) and N,N-bis(1-methylethyl)ethanamine (0.0062 mol) in CH$_2$Cl$_2$ (20 ml). The mixture was stirred at RT for 12 hours, then poured out into H$_2$0 and decanted. The organic layer was washed with H$_2$O dried, filtered and the solvent was evaporated. The residue was purified by column chromatography over silica gel (eluent: CH$_2$Cl$_2$/CH$_3$OH 98/2). The pure fractions were collected and the solvent was evaporated. The residue was crystallized from 2-propanone and diethyl ether. The precipitate was filtered off and dried, yielding 0.2 g (18%) of N-[5-[2-[1-[2,6-dichloro-4-(4,5-dihydro-3,5-dioxo-1,2,4-triazine-2(3H)-yl)phenyl]-1-methylethyl]-4-thiazolyl]-2-thienyl]-N-(methylsulfonyl)methanesulfonamide (comp. 81).

The following tables list compounds of formula (I) which were prepared analogous to one of the above examples.

TABLE 2

[Structure: thiazole with $R^{11a}$ at 4-position and $R^{11b}$ at 5-position, connected via C(CH$_3$)$_2$ to a 2,6-dichlorophenyl bearing a 4,5-dihydro-3,5-dioxo-1,2,4-triazin-2(3H)-yl group]

| Co. No. | Ex. No. | $R^{11a}$ | $R^{11b}$ | Salt/melting point |
|---|---|---|---|---|
| 1 | B.1a | phenyl | H | mp. 120° C. |
| 2 | B.1a | phenyl | (CH$_3$)$_2$N—CH$_2$— | HCl (1:1) |
| 3 | B.2 | 3-chlorophenyl | CH$_3$ | |
| 4 | B.2 | 2-chlorophenyl | H | |
| 5 | B.2 | 2-thienyl | H | mp. 188° C. |
| 6 | B.2 | phenyl | C$_2$H$_5$—O—CO— | mp. 203° C. |
| 7 | B.2 | 4-pyridinyl | H | |
| 8 | B.2 | 3-chlorophenyl | H | |
| 9 | B.2 | phenyl | C$_2$H$_5$—O—CO—CH$_2$— | mp. 148° C. |
| 10 | B.2 | phenyl | CH$_3$ | |
| 11 | B.2 | 2-fluorophenyl | H | |
| 12 | B.2 | 4-bromophenyl | H | |
| 13 | B.2 | 2,6-difluorophenyl | H | |
| 14 | B.2 | phenyl | 4-morpholinyl | |
| 15 | B.2 | 2-fluorophenyl | CH$_3$ | |
| 16 | B.2 | phenyl | 1-methyl-4-piperazinyl | |
| 17 | B.2 | 3-fluorophenyl | CH$_3$ | |
| 18 | B.2 | 2,4-difluorophenyl | H | |
| 19 | B.3a | phenyl | HOOC—CH$_2$— | |
| 20 | B.3b | phenyl | 4-morpholinyl-CO—CH$_2$— | |
| 21 | B.3b | phenyl | CH$_3$-N(piperazinyl)-CO—CH$_2$— | |
| 22 | B.3b | phenyl | 4-hydroxypiperidinyl-CO—CH$_2$— | |
| 23 | B.2 | phenyl | phenyl | |
| 24 | B.3b | phenyl | [1,4'-bipiperidin]-1'-yl-CO—CH$_2$— | |
| 25 | B.2 | phenyl | phenyl-CO— | |
| 26 | B.2 | 2-methoxyphenyl | H | |
| 27 | B.2 | 2-chlorophenyl | CH$_3$ | |
| 28 | B.2 | 3-fluorophenyl | H | |
| 29 | B.5 | phenyl | phenyl-CH(OH)— | |
| 30 | B.2 | phenyl | CH$_3$—O—CH$_2$— | |
| 31 | B.2 | CH$_3$ | phenyl | |
| 32 | B.2 | 2-chlorophenyl | phenyl | |
| 33 | B.2 | phenyl | 3-pyridinyl | |
| 34 | B.2 | 2-fluorophenyl | phenyl | |
| 35 | B.4 | phenyl | benzyl-piperazinyl-CO—CH$_2$— | |

TABLE 2-continued

[Structure: central phenyl ring with two Cl substituents, attached to a 1,2,4-triazine-3,5(2H,4H)-dione on one side and a C(CH$_3$)$_2$ group linked to a thiazole (bearing R$^{11a}$ and R$^{11b}$) on the other side.]

| Co. No. | Ex. No. | R$^{11a}$ | R$^{11b}$ | Salt/melting point |
|---|---|---|---|---|
| 36 | B.3b | phenyl | [1-methylpiperidin-4-yl-N(CH$_3$)-C(=O)-CH$_2$---] | |
| 37 | B.2 | 3-chlorophenyl | phenyl | |
| 38 | B.2 | 2-methylphenyl | phenyl | |
| 39 | B.2 | phenyl | 1-(CH$_3$—CO)-4-piperidinyl- | |
| 40 | B.2 | 2-methylphenyl | H | mp. 225° C. |
| 41 | B.6a | phenyl | Br—CH$_2$— | |
| 42 | B.6b | phenyl | H$_3$CO—(CH$_2$)$_2$—N(piperazine)N—CH$_2$--- | |
| 43 | B.2 | phenyl | phenylmethyl | |
| 44 | B.2 | 3-(CH$_3$OCH$_2$)phenyl | CH$_3$— | |
| 45 | B.2 | phenyl | 2-phenylethyl | |
| 46 | B.2 | 2-chlorophenyl | HCO— | |
| 47 | B.6b | phenyl | phenyl-CH$_2$—N(piperazine)N—CH$_2$--- | HCl (1:2); H$_2$O (1:1) |
| 48 | B.2 | 4-phenylphenyl- | C$_2$H$_5$— | |
| 49 | B.2 | phenyl | 3-(NO$_2$)-phenyl | |
| 50 | B.7a | phenyl | 3-(NH$_2$)-phenyl | |
| 51 | B.7b | phenyl | 3-(CH$_3$—CO—NH)-phenyl | |
| 52 | B.6b | phenyl | CH$_3$—N(piperidin-4-yl)—N(CH$_3$)—CH$_2$--- | acetate (1:2) |
| 53 | B.6b | phenyl | [piperidin-1-yl]-[piperidin-4-yl]—N—CH$_2$--- | acetate (2:1) |
| 54 | B.7c | phenyl | 3-(H$_2$N—CO—NH)-phenyl- | |
| 55 | B.2 | phenyl | 3-methoxyphenyl | |
| 56 | B.2 | 2-chlorophenyl | 3-HOOC-phenyl | mp. 266° C. |
| 57 | B.2 | 2-chlorophenyl | 3-CN-phenyl | |
| 58 | B.8a | phenyl | 3-OH-phenyl | |
| 59 | B.9a | 2-chlorophenyl | 3-(HO—CH$_2$)-phenyl- | |
| 60 | B.7d | phenyl | 3-(NH$_2$—SO$_2$—NH)-phenyl- | |
| 61 | B.14 | 2-chlorophenyl | [4-methylpiperazin-1-yl-C(=O)-(3-phenyl)---] | |
| 62 | B.11 | 2-chlorophenyl | 3-(H$_2$N—CO)-phenyl- | |

TABLE 2-continued

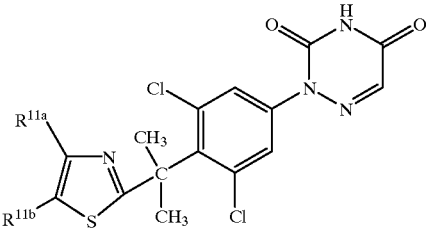

| Co. No. | Ex. No. | R11a | R11b | Salt/melting point |
|---|---|---|---|---|
| 63 | B.10 | 2-chlorophenyl | 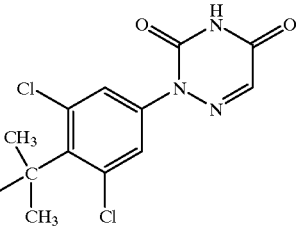 | |
| 64 | B.7e | phenyl | 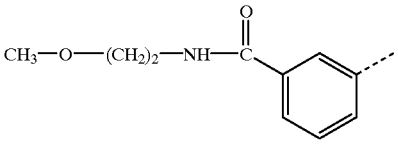 | 2-propanolate (1:1) |
| 65 | B.2 | 2-chlorophenyl | 3-[(CH$_3$)$_2$—CH—O—CO]phenyl | |
| 66 | B.8b | phenyl | 3-(NH$_2$—SO$_2$—O)phenyl | |
| 67 | B.9b | 2-chlorophenyl | 3-HCO-phenyl | |
| 68 | B.9e | 2-chlorophenyl | 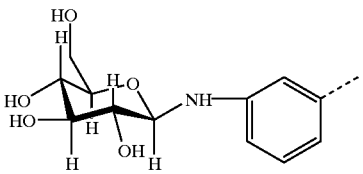 | |
| 69 | B.9c | 2-chlorophenyl | 3-(CH$_3$OC$_2$H$_5$—NH—CH$_2$)-phenyl | HCl (1:1) |
| 70 | B.15a | phenyl | 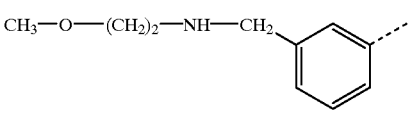 | |
| 71 | B.15b | phenyl | 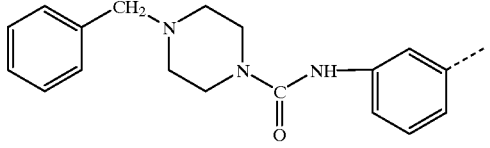 | H$_2$O (1:1) |
| 72 | B.2 | 3-thienyl | H | mp. 115° C. |
| 73 | B.2 | 5-chloro-2-thienyl | H | mp. 220° C. |
| 74 | B.2 | 5-nitro-2-thienyl | H | mp. 235° C. |
| 75 | B.2 | 3-methyl-2-thienyl | H | mp. 170° C. |
| 76 | B.2 | 5-methyl-2-thienyl | H | mp. 160° C. |
| 77 | B.2 | 5-bromo-2-thienyl | H | mp. 192° C. |
| 78 | B.2 | 5-cyano-2-thienyl | H | mp. 230° C. |
| 79 | B.2 | 3-benzo[b]thienyl | H | mp. 151° C. |
| 80 | B.17a | 5-amino-2-thienyl | H | |
| 81 | B.17b | 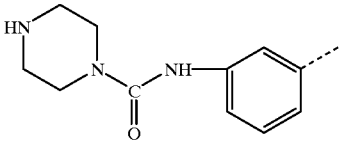 | H | mp. 226° C. |

TABLE 2-continued

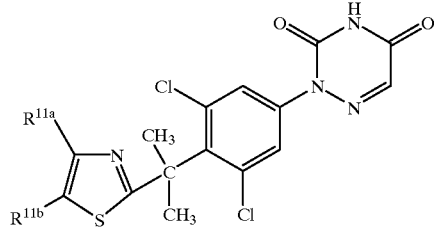

| Co. No. | Ex. No. | R$^{11a}$ | R$^{11b}$ | Salt/melting point |
|---|---|---|---|---|
| 82 | B.2 | 3-pyridinyl | H | mp. 165° C. |
| 83 | B.2 | 2-furanyl | H | mp. 110° C. |
| 84 | B.2 | 5-(2-thienyl)-2-thienyl | H | mp. 126° C. |
| 85 | B.2 | 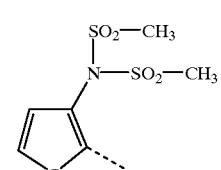 | H | mp. 225° C. |
| 110 | B.2 | 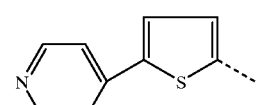 | H | mp. >250° C. |
| 111 | B.16a | 2-methyl-5-thienyl | Br | mp. 186° C. |
| 112 | B.2 | 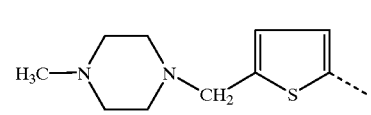 | H | mp. 250° C. |
| 113 | B.2 | 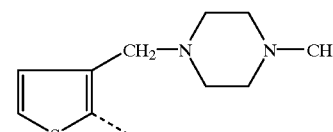 | H | mp. 130° C. H$_2$O (1:1) |
| 114 | B.2 | 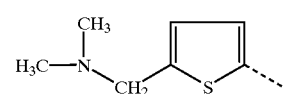 | H | mp. 223° C. |
| 115 | B.2 | 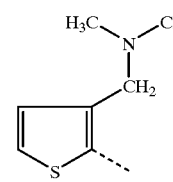 | H | mp. >250° C. |
| 116 | B.19a | phenyl | 1,1-dimethylethoxycarbonyl | |
| 117 | B.19b | phenyl | carboxyl | mp. 230° C. |
| 118 | B.2 | 2-thienyl | ethoxycarbonylmethyl | mp. 126° C. |
| 119 | B.2 | 2-thienyl | 1,1-dimethylethoxycarbonyl | mp. 80° C. |
| 120 | B.19b | 2-thienyl | carboxyl | mp. >250° C. |
| 121 | B.3a | 2-thienyl | carboxylmethyl | mp. 192° C. |
| 122 | B.2 | phenyl | 1-methylethoxycarbonyl | mp. 225° C. |

TABLE 3

[Structure: 1,2,4-triazine-3,5-dione N-substituted with 3,5-dichloro-4-[2-(oxadiazol-3-yl)propan-2-yl]phenyl group, where the oxadiazole bears R^11a]

| Co. No. | Ex. No. | R^11a | Salt/melting point |
|---------|---------|-------|---------------------|
| 86 | B.1a | 2-fluorophenyl | |
| 87 | B.1a | 2-methylphenyl | |
| 88 | B.1a | phenyl | |
| 89 | B.1a | 2-chlorophenyl | |
| 90 | B.1a | 3-fluorophenyl | |
| 91 | B.1a | 3-methylphenyl | |
| 92 | B.1a | 2-thienyl | |
| 93 | B.1a | 3-chlorophenyl | |
| 94 | B.16b | CH₃–N(piperazine)N–CH₂–(2-phenyl) | HCl (1:3) |
| 95 | B.16a | 2-(bromomethyl)phenyl | |
| 96 | B.1a | 4-fluorophenyl | |
| 97 | B.1a | 4-pyridinyl | HCl (1:1) |
| 98 | B.1a | 2-pyridinyl | |
| 123 | B.16 | H₃C–C(O)–N(piperazine)N–CH₂–(2-phenyl) | |
| 124 | B.1 | 3-pyridinyl | |
| 125 | B.1 | 4-methylphenyl | |
| 126 | B.1 | 3-carboxylphenyl | |
| 127 | B.9a | 3-(hydroxymethyl)phenyl | |
| 128 | B.23 | 3-(chloromethyl)phenyl | |
| 129 | B.6 | H₃C–C(O)–N(piperazine)N–CH₂–(3-phenyl) | |
| 130 | B.16 | H₃C–O–CH₂–CH₂–N(CH₃)–CH₂–(2-phenyl) | HCl (1:1) |
| 131 | B.16 | (CH₃)₃C–O–C(O)–N(piperazine)N–CH₂–(2-phenyl) | HBr (1:1) |

TABLE 3-continued
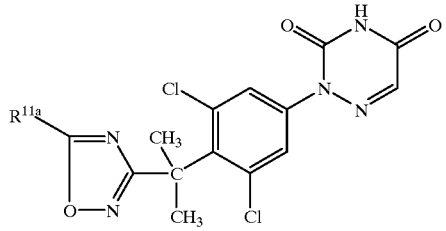
| Co. No. | Ex. No. | R$^{11a}$ | Salt/melting point |
|---|---|---|---|
| 132 | B.22 | 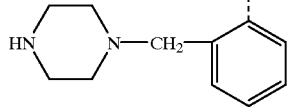 | HCl (1:2) |
| 133 | B.25 | 3-(methoxycarbonyl)phenyl | |
| 134 | B.1 | 4-carboxylphenyl | |
| 135 | B.25 | 4-(methoxycarbonyl)phenyl | mp. 210° C. |
| 136 | B.9a | 4-(hydroxymethyl)phenyl | |
| 137 | B.23 | 4-(chloromethyl)phenyl | |
| 138 | B.6 | 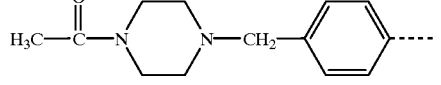 | |
| 139 | B.16 | 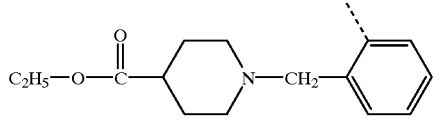 | HCl (1:1) |
| 140 | B.16 | 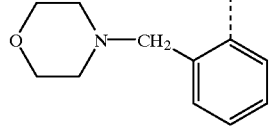 | HCl (1:1) |
| 141 | B.2 | 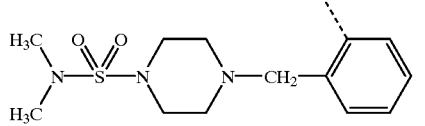 | HCl (1:1); H$_2$O (1:2) |
| 142 | B.16 | 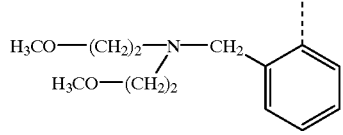 | HCl (1:1); H$_2$O (1:1) |

TABLE 3-continued
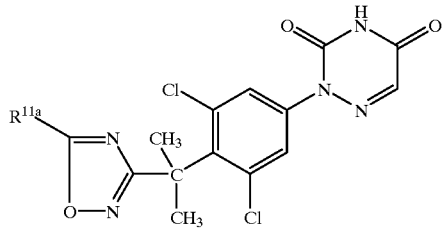
| Co. No. | Ex. No. | R[11a] | Salt/melting point |
|---|---|---|---|
| 143 | B.16 | 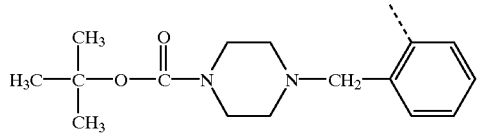 | |
| 144 | B.1 | 3-fluoro-2-methylphenyl | |
| 145 | B.1 | 5-carboxyl-2-pyridinyl | |
| 146 | B.25 | 5-(methoxycarbonyl)-2-pyridinyl | mp. 238° C. |
| 147 | B16 | 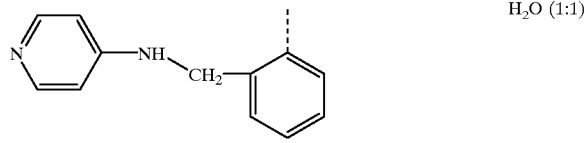 | H₂O (1:1) |
| 148 | B.16 | 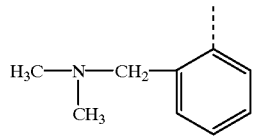 | |
| 149 | B.16 | 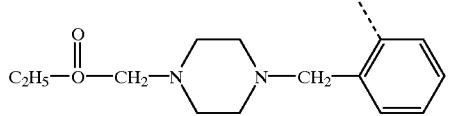 | |
| 150 | B.1 | 2-methyl-3-pyridinyl | |
| 151 | B.1 | 2,4-dimethyl-3-pyridinyl | CH₂Cl₂ (1:1) |
| 152 | B.1 | 4-piperidinyl | HCl (1:1) |
| 153 | B.1 | 2-trifluoromethylphenyl | |
| 154 | B.6 | 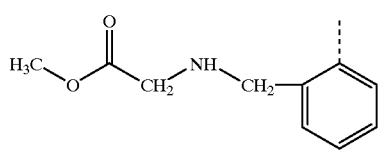 | |
| 155 | B.9a | 2-(hydroxymethyl)phenyl | |
| 156 | B.1 | 2-carboxylphenyl | |
| 157 | B.25 | 2-(ethoxycarbonyl)phenyl | |
| 158 | B.21 | 2-(carboxylmethyl)phenyl | |

TABLE 4
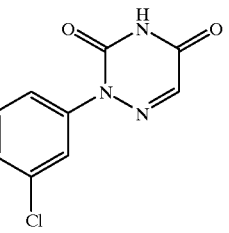
| Co. No. | Ex. No. | R² |
|---|---|---|
| 99 | B.12 | NH₂—C(=S)— |
| 100 | B.2 | 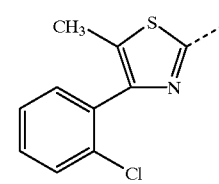 |
| 101 | B.13 | (3-pyridinyl)-CO— |
TABLE 5
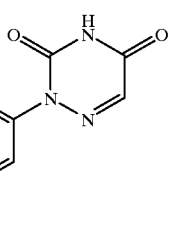
| Co. No. | Ex. No. | R$^{1a}$ | R$^{1b}$ | Z | Salt/melting point |
|---|---|---|---|---|---|
| 102 | B.1a | H | H | 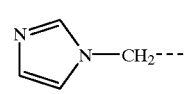 | HCl (1:1); mp. 263.3° C. |
| 103 | B.1a | Cl | Cl | 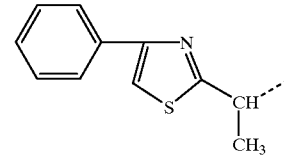 | mp. 177° C. |
| 104 | B.1a | Cl | H | 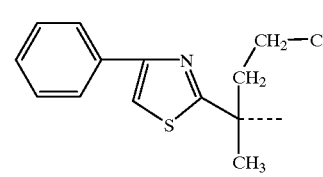 | mp. 10° C. |

TABLE 5-continued
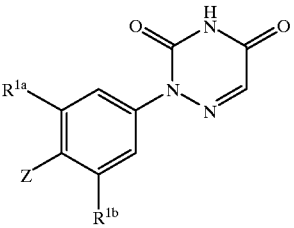
| Co. No. | Ex. No. | R¹ᵃ | R¹ᵇ | Z | Salt/melting point |
|---|---|---|---|---|---|
| 105 | B.2 | Cl | H | 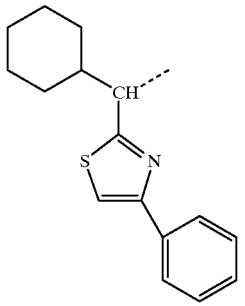 | mp. 216° C. |
| 106 | B.1a | Cl | Cl | 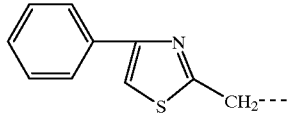 | |
| 107 | B.1b | Cl | Cl | 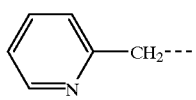 | HCl (1:1); H₂O (1:1);. 240° C. |
| 108 | B.1a | Cl | Cl | 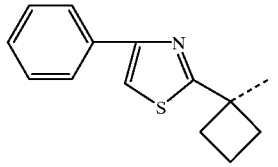 | ethanolate (1:1) |
| 109 | B.1a | Cl | Cl | 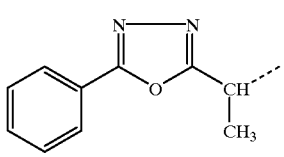 | |
| 159 | B.18 | Cl | H | 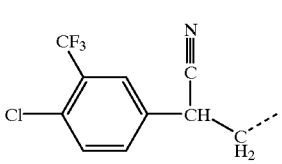 | mp. 182° C. |

TABLE 5-continued
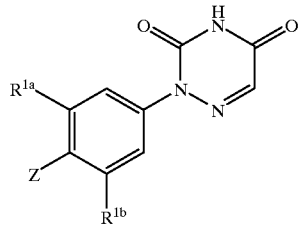
| Co. No. | Ex. No. | R¹ᵃ | R¹ᵇ | Z | Salt/melting point |
|---|---|---|---|---|---|
| 160 | B.2 | Cl | H | 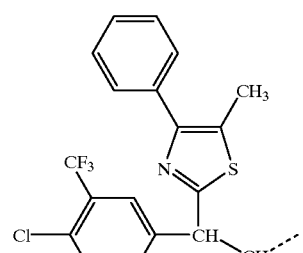 | mp. 190° C. |
| 161 | B.2 | Cl | H | 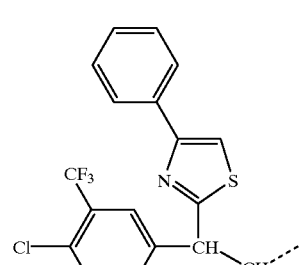 | mp. 150° C. |
| 162 | B.20 | Cl | H | 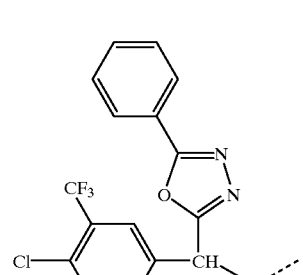 | mp. 188° C. |
| 163 | B.24 | Cl | Cl | 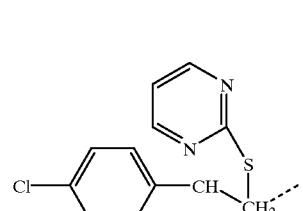 | |
| 164 | B.20 | Cl | Cl | 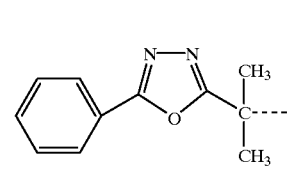 | mp. 292° C. |

C. Pharmacological Example

EXAMPLE C.1: IN VITRO INHIBITION OF IL-5 PRODUCTION IN HUMAN BLOOD

Human Whole Blood Stimulation

Peripheral blood from healthy male donors was drawn into heparinized syringes (12.5 U heparin/ml). Blood samples were three-fold diluted in RMPI 1640 medium (Life Technologies, Belgium) supplemented with 2 mM L-glutamine, 100 U/ml penicillin and 100 µg/ml streptomycin, and 300 µl fractions were distributed in 24-well multidisc plates. Blood samples were preincubated (60 minutes at 37° C.) in a humidified 6% $CO_2$-atmosphere with 100 µl of drug solvent (final concentration 0.02% dimethylsulfoxide in RPMI 1640) or with 100 µl of an appropriate dose of test compound before being stimulated by the addition of 100 µl of phytohemagglutinin HA17 (Murex, UK) at a final concentration of 2 µg/ml. After 48 hours, cell-free supernatant fluids were collected by centrifugation and stored at −70° C. until tested for the presence of IL-5.

IL-5 Measurements

IL-5 measurements were conducted as described in Van Wauwe et al. (1996, Inflamm Res, 45, 357–363) on page 358 using ELISA.

Table 6 lists the percentage inhibition of IL-5 production (column "% inh") at a test dose of $1\times10^{-6}$ M, or in case the percentage inhibition is marked with an "*" $1\times10^{-5}$ M, for the compounds of the present invention.

TABLE 6

| Co. No. | % inh. |
|---|---|
| 1 | 90.5 |
| 2 | 92 |
| 3 | 92 |
| 4 | 94 |
| 5 | 90 |
| 6 | 94 |
| 7 | 88 |
| 8 | 85 |
| 9 | 88 |
| 10 | 85 |
| 11 | 88 |
| 12 | 70 |
| 13 | 75 |
| 14 | 78 |
| 15 | 81 |
| 16 | 57 |
| 17 | 94 |
| 18 | 91 |
| 19 | 13 |
| 20 | 80 |
| 21 | 52 |
| 22 | 18 |
| 23 | 91 |
| 24 | 32 |
| 25 | 79 |
| 26 | 84 |
| 27 | 77 |
| 28 | 83 |
| 29 | 71 |
| 30 | 93 |
| 31 | 87 |
| 32 | 91 |
| 33 | 90 |
| 34 | 93 |
| 35 | 63 |
| 36 | 9 |
| 37 | 92 |
| 38 | 93 |
| 39 | 72 |
| 40 | 89 |
| 42 | 26 |
| 43 | 86 |
| 44 | 81 |
| 45 | 85 |
| 46 | 44 |
| 47 | 6 |
| 48 | 58 |
| 49 | 95 |
| 50 | 91 |
| 51 | 73 |
| 52 | 45 |
| 53 | 22 |
| 54 | 61 |
| 55 | 92 |
| 56 | −4 |
| 57 | 85 |
| 58 | 84 |
| 59 | 82 |
| 60 | 28 |
| 61 | 29 |
| 62 | 53 |
| 63 | 38 |
| 64 | 86 |
| 65 | 36 |
| 66 | 53 |
| 69 | 45 |
| 71 | 27 |
| 72 | 84 |
| 73 | 84 |
| 74 | 76 |
| 75 | 91 |
| 76 | 75 |
| 77 | 84 |
| 78 | 79 |
| 79 | 75 |
| 81 | 34 |
| 82 | 85 |
| 83 | 78 |
| 84 | 14 |
| 85 | 33 |
| 86 | 88 |
| 87 | 89 |
| 88 | 94 |
| 89 | 84 |
| 90 | 91 |
| 91 | 81 |
| 92 | 80 |
| 93 | 84 |
| 94 | 34 |
| 96 | 82 |
| 97 | 90 |
| 98 | 58 |
| 100 | 15 |
| 101 | 19 |
| 102 | 8.5* |
| 103 | 60 |
| 104 | 73 |
| 105 | 58.5 |
| 106 | 3 |
| 107 | 14 |
| 108 | 51 |
| 109 | 62 |
| 110 | 72 |
| 111 | 88 |
| 112 | 39 |
| 113 | 28 |
| 114 | 29 |
| 115 | 15 |
| 116 | 89 |
| 117 | −7 |
| 118 | 78 |
| 119 | 93 |
| 120 | 8 |
| 121 | −3 |
| 122 | 94 |
| 123 | 89 |

TABLE 6-continued

| Co. No. | % inh. |
|---|---|
| 124 | 86 |
| 125 | 43 |
| 127 | 67 |
| 129 | 83 |
| 130 | 59 |
| 132 | 16 |
| 133 | 55 |
| 135 | 11 |
| 138 | −19 |
| 139 | 85 |
| 140 | 92 |
| 141 | 70 |
| 142 | 15 |
| 143 | 77 |
| 144 | 90 |
| 146 | 4 |
| 147 | −2 |
| 148 | 44 |
| 149 | 80 |
| 150 | 73 |
| 151 | 74 |
| 152 | 21 |
| 153 | 77 |
| 154 | 44 |
| 155 | 85 |
| 158 | 3 |
| 159 | 62 |
| 160 | 75 |
| 161 | 80 |
| 162 | 62 |
| 163 | 54 |
| 164 | 90 |

D. Composition Examples

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

EXAMPLE D.1: FILM-COATED TABLETS

Preparation of Tablet Core

A mixture of A.I. (100 g), lactose (570 g) and starch (200 g) was mixed well and thereafter humidified with a solution of sodium dodecyl sulfate (5 g) and polyvinyl-pyrrolidone (10 g) in about 200 ml of water. The wet powder mixture was sieved, dried and sieved again. Then there was added microcrystalline cellulose (100 g) and hydrogenated vegetable oil (15 g). The whole was mixed well and-compressed into tablets, giving 10.000 tablets, each comprising 10 mg of the active ingredient.

Coating

To a solution of methyl cellulose (10 g) in denaturated ethanol (75 ml) there was added a solution of ethyl cellulose (5 g) in $CH_2Cl_2$ (150 ml). Then there were added $CH_2Cl_2$ (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

EXAMPLE D.2: 2% TOPICAL CREAM

To a solution of hydroxypropyl B-cyclodextrine (200 mg) in purified water is added A.I. (20 mg) while stirring. Hydrochloric acid is added until complete dissolution and next sodium hydroxide is added until pH 6.0. While stirring, glycerol (50 mg) and polysorbate 60 (35 mg) are added and the mixture is heated to 70° C. The resulting mixture is added to a mixture of mineral oil (100 mg), stearyl alcohol (20 mg), cetyl alcohol (20 mg), glycerol monostearate (20 mg) and sorbate 60 (15 mg) having a temperature of 70° C. while mixing slowly. After cooling down to below 25° C., the rest of the purified water q.s. ad 1 g is added and the mixture is mixed to homogenous.

What is claimed is:

1. A compound having the formula

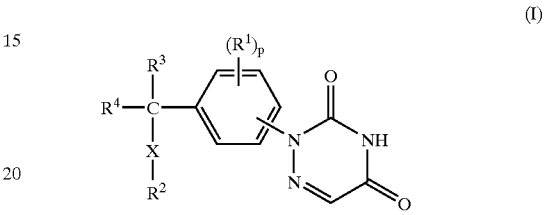

(I)

a N-oxide, a pharmaceutically acceptable addition salt or a stereochemically isomeric form thereof, wherein:

p represents an integer being 0, 1, 2, 3 or 4;

X represents O, S, $NR^5$ or a direct bond;

Y represents O, S, $NR^5$, or $S(O)_2$;

each $R^1$ independently represents $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, $Het^3$, $R^6$, $NR^7R^8$ or $C_{1-4}$alkyl substituted with $Het^3$, $R^6$ or $NR^7R^8$;

$R^2$ represents $Het^1$ or $C_{1-6}$alkyl substituted with one or two substituents selected from hydroxy, cyano, amino, mono- or di($C_{1-4}$alkyl)amino, $C_{1-6}$alkyloxy, $C_{1-6}$alkylsulfonyloxy, $C_{1-6}$alkyloxycarbonyl, $C_{3-7}$cycloalkyl, aryl, aryloxy, arylthio, $Het^1$, $Het^1$oxy, and $Het^1$thio; and if X is O, S or $NR^5$, then $R^2$ may also represent aminocarbonyl, aminothiocarbonyl, $C_{1-4}$alkylcarbonyl, $C_{1-4}$alkylthiocarbonyl, arylcarbonyl, arylthiocarbonyl, $Het^1$carbonyl or $Het^1$thiocarbonyl;

$R^3$ represents hydrogen, $C_{1-6}$alkyl or $C_{3-7}$cycloalkyl;

$R^4$ represents hydrogen, $C_{1-6}$alkyl or $C_{3-7}$cycloalkyl; or $R^3$ and $R^4$ taken together form a $C_{2-6}$alkanediyl;

$R^5$ represents hydrogen or $C_{1-4}$alkyl;

each $R^6$ independently represents $C_{1-6}$alkylsulfonyl, aminosulfonyl, mono- or di($C_{1-4}$alkyl)aminosulfonyl, mono- or di(benzyl)aminosulfonyl, polyhalo$C_{1-6}$alkylsulfonyl, $C_{1-6}$alkylsulfinyl, phenyl$C_{1-4}$alkylsulfonyl, piperazinylsulfonyl, aminopiperidinylsulfonyl, piperidinylaminosulfonyl, N-$C_{1-4}$alkyl-N-piperidinylaminosulfonyl or mono-or di($C_{1-4}$alkyl)amino$C_{1-4}$alkylsulfonyl;

each $R^7$ and each $R^8$ are independently selected from the group consisting of: hydrogen, $C_{1-4}$alkyl, hydroxy$C_{1-4}$alkyl, dihydroxy$C_{1-4}$alkyl, aryl, aryl$C_{1-4}$alkyl, $C_{1-4}$alkyloxy$C_{1-4}$alkyl, $C_{1-4}$alkylcarbonyl, aminocarbonyl, arylcarbonyl, $Het^3$carbonyl, $C_{1-4}$alkylcarbonyloxy-$C_{1-4}$alkylcarbonyl, hydroxy$C_{1-4}$alkylcarbonyl, $C_{1-4}$alkyloxycarbonylcarbonyl, mono- or di($C_{1-4}$alkyl)amino$C_{1-4}$alkyl, arylaminocarbonyl, $Het^3$aminocarbonyl, arylaminothiocarbonyl, $Het^3$aminothiocarbonyl, $C_{3-7}$cycloalkyl, pyridinyl$C_{1-4}$alkyl, $C_{1-4}$alkanediyl-C(=O)—O—$R^{14}$, —C(=O)—

O—R$^{14}$, —Y—C$_{1-4}$alkanediyl-C(=O)—O—R$^{14}$, Het$^3$, Het$^4$ and R$^6$;

R$^9$ and R$^{10}$ are each independently selected from the group consisting of: hydrogen, C$_{1-4}$alkyl, hydroxyC$_{1-4}$alkyl, dihydroxyC$_{1-4}$alkyl, phenyl, phenylC$_{1-4}$alkyl, C$_{1-4}$alkyloxyC$_{1-4}$alkyl, C$_{1-4}$alkylcarbonyl, aminocarbonyl, phenylcarbonyl, Het$^3$carbonyl, C$_{1-4}$alkylcarbonyloxyC$_{1-4}$alkylcarbonyl, hydroxyC$_{1-4}$alkylcarbonyl, C$_{1-4}$alkyloxycarbonylcarbonyl, mono- or di(C$_{1-4}$alkyl)aminoC$_{1-4}$alkyl, phenylaminocarbonyl, phenylaminothiocarbonyl, Het$^3$aminocarbonyl, Het$^3$aminothiocarbonyl, C$_{3-7}$cycloalkyl, pyridinylC$_{1-4}$alkyl, C$_{1-4}$alkanediyl-C(=O)—O—R$^{14}$, —C(=O)—O—R$^{14}$, —Y—C$_{1-4}$alkanediyl-C(=O)—O—R$^{14}$, Het$^3$, Het$^4$ and R$^6$;

each R$^{11}$ independently being selected from the group consisting of: hydroxy, mercapto, cyano, nitro, halo, trihalomethyl, C$_{1-4}$alkyloxy, formyl, trihaloC$_{1-4}$alkylsulfonyloxy, R$^6$, NR$^7$R$^8$, C(=O)NR$^7$R$^8$, —C(=O)—O—R$^{14}$, —Y—C$_{1-4}$alkanediyl-C(=O)—O—R$^{14}$, aryl, aryloxy, arylcarbonyl, C$_{3-7}$cycloalkyl, C$_{3-7}$cycloalkyloxy, phthalimide-2-yl, Het$^3$ and C(=O)Het$^3$;

R$^{12}$ and R$^{13}$ are each independently selected from the group consisting of: hydrogen, C$_{1-4}$alkyl, hydroxyC$_{1-4}$alkyl, dihydroxyC$_{1-4}$alkyl, phenyl, phenylC$_{1-4}$alkyl, C$_{1-4}$alkyloxyC$_{1-4}$alkyl, C$_{1-4}$alkylcarbonyl, phenylcarbonyl, C$_{1-4}$alkylcarbonyloxyC$_{1-4}$alkylcarbonyl, hydroxyC$_{1-4}$alkylcarbonyl, C$_{1-4}$alkyloxycarbonylcarbonyl, mono- or di(C$_{1-4}$alkyl)aminoC$_{1-4}$alkyl, phenylaminocarbonyl, phenylaminothiocarbonyl, C$_{3-7}$cycloalkyl, pyridinylC$_{1-4}$alkyl, C$_{1-4}$alkanediyl-C(=O)—O—R$^{14}$, —C(=O)—O—R$^{14}$, —Y—C$_{1-4}$alkanediyl-C(=O)—O—R$^{14}$ and R$^6$;

each R$^{14}$ independently represents hydrogen, C$_{1-4}$alkyl, C$_{3-7}$cycloalkyl, aminocarbonylmethylene or mono-or di(C$_{1-4}$alkyl)aminocarbonylmethylene;

aryl represents phenyl optionally substituted with one, two or three substituents each independently selected from nitro, azido, cyano, halo, hydroxy, C$_{1-4}$alkyl, C$_{3-7}$cycloalkyl, C$_{1-4}$alkyloxy, formyl, polyhaloC$_{1-4}$alkyl, NR$^9$R$^{10}$, C(=O)NR$^9$R$^{10}$, C(=O)—O—R$^{14}$, R$^6$, —O—R$^6$, phenyl, Het$^3$, C(=O)Het$^3$ and C$_{1-4}$alkyl substituted with hydroxy, C$_{1-4}$alkyloxy, C(=O)—O—R$^{14}$, —Y—C$_{1-4}$alkanediyl-C(=O)—O—R$^{14}$, Het$^3$ or NR$^9$R$^{10}$;

Het$^1$ represents a heterocycle selected from the group consisting of: pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from Het$^2$, R$^{11}$ and C$_{1-4}$alkyl optionally substituted with one or two substituents independently selected from Het$^2$ and R$^{11}$; provided Het$^1$ is other than 2-substituted-pyridin-5-yl;

Het$^2$ represents a heterocycle selected from the group consisting of: pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from Het$^4$, R$^{11}$ and C$_{1-4}$alkyl optionally substituted with one or two substituents independently selected from Het$^4$ and R$^{11}$;

Het$^3$ represents a monocyclic heterocycle selected from the group consisting of: pyrrolidinyl, piperidinyl, piperazinyl, morpholinyl, thiomorpholinyl and tetrahydropyranyl; wherein said monocyclic heterocycles each independently may optionally be substituted with, where possible, one, two, three or four substituents each independently selected from hydroxy, C$_{1-4}$alkyl, C$_{1-4}$alkyloxy, C$_{1-4}$alkylcarbonyl, piperidinyl, NR$^{12}$R$^{13}$, C(=O)—O—R$^{14}$, R$^6$ and C$_{1-4}$alkyl substituted with one or two substituents independently selected from hydroxy, C$_{1-4}$alkyloxy, phenyl, C(=O)—O—R$^{14}$, —Y—C$_{1-4}$alkanediyl-C(=O)—O—R$^{14}$, R$^6$ and NR$^{12}$R$^{13}$;

Het$^4$ represents a monocyclic heterocycle selected from the group consisting of: pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl.

2. A compound as claimed in claim 1 wherein:

each R$^7$ and each R$^8$ are independently selected from the group consisting of: hydrogen, C$_{1-4}$alkyl, hydroxyC$_{1-4}$alkyl, dihydroxyC$_{1-4}$alkyl, aryl, arylC$_{1-4}$alkyl, C$_{1-4}$alkyloxyC$_{1-4}$alkyl, C$_{1-4}$alkylcarbonyl, aminocarbonyl, arylcarbonyl, Het$^3$carbonyl, C$_{1-4}$alkylcarbonyloxy-C$_{1-4}$alkylcarbonyl, hydroxyC$_{1-4}$alkylcarbonyl, C$_{1-4}$alkyloxycarbonylcarbonyl, mono- or di(C$_{1-4}$alkyl)aminoC$_{1-4}$alkyl, arylaminocarbonyl, arylaminothiocarbonyl, Het$^3$aminocarbonyl, Het$^3$aminothiocarbonyl, C$_{3-7}$cycloalkyl, pyridinylC$_{1-4}$alkyl, C$_{1-4}$alkanediyl-C(=O)—O—R$^{14}$, —C(=O)—O—R$^{14}$, —Y—C$_{1-4}$alkanediyl-C(=O)—O—R$^{14}$, Het$^3$ and R$^6$;

R$^9$ and R$^{10}$ are each independently selected from the group consisting of: hydrogen, C$_{1-4}$alkyl, hydroxyC$_{1-4}$alkyl, dihydroxyC$_{1-4}$alkyl, phenyl, phenylC$_{1-4}$alkyl, C$_{1-4}$alkyloxyC$_{1-4}$alkyl, C$_{1-4}$alkylcarbonyl, aminocarbonyl, phenylcarbonyl, Het$^3$carbonyl, C$_{1-4}$alkylcarbonyloxyC$_{1-4}$alkylcarbonyl, hydroxyC$_{1-4}$alkylcarbonyl, C$_{1-4}$alkyloxycarbonylcarbonyl, mono- or di(C$_{1-4}$alkyl)aminoC$_{1-4}$alkyl, phenylaminocarbonyl, phenylaminothiocarbonyl, Het$^3$aminocarbonyl, Het³aminothiocarbonyl, $C_{3-7}$cycloalkyl, pyridinyl$C_{1-4}$alkyl, $C_{1-4}$alkanediyl-C(=O)—O—R¹⁴, —C(=O)—O—R¹⁴, —Y—$C_{1-4}$alkanediyl-C(=O)—O—R¹⁴, Het³ and R⁶;

R¹¹ is being selected from the group consisting of: hydroxy, mercapto, cyano, nitro, halo, trihalomethyl, $C_{1-4}$alkyloxy, formyl, trihalo$C_{1-4}$alkylsulfonyloxy, R⁶, NR⁷R⁸, C(=O)NR⁷R⁸, —C(=O)—O—R¹⁴, aryl, aryloxy, arylcarbonyl, $C_{3-7}$cycloalkyl, $C_{3-7}$cycloalkyloxy, phthalimide-2-yl, Het³, Het⁴ and C(=O)Het³; and Het² represents a heterocycle selected from the group consisting of: pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from R¹¹ and $C_{1-4}$alkyl optionally substituted with one or two substituents independently selected from R¹¹.

3. A compound of the formula:

2-[3,5-dichloro-4-[1-methyl-1-(4-phenyl-2-thiazolyl)ethyl]phenyl]-1,2,4-triazine-3,5(2H,4H)-dione;

2-[3,5-dichloro-4-[1-[4-(3-chlorophenyl)-5-methyl-2-thiazolyl]-1-methylethyl]-phenyl]-1,2,4-triazine-3,5(2H,4H)-dione;

2-[3,5-dichloro-4-[1-methyl-1-(5-phenyl-1,2,4-oxadiazol-3-yl)ethyl]phenyl]-1,2,4-triazine-3,5(2H,4)-dione;

2-[3,5-dichloro-4-[1-(4,5-diphenyl-2-thiazolyl)-1-methylethyl]phenyl]-1,2,4-triazine-3,5(2H,4H)-dione;

2-[3,5-dichloro-4-[1-methyl-1-[5-(2-methylphenyl)-1,2,4-oxadiazol-3-yl]ethyl]-phenyl]-1,2,4-triazine-3,5(2H,4H)-dione;

2-[3,5-dichloro-4-[1-methyl-1-(4-methyl-5-phenyl-2-thiazolyl)ethyl]phenyl]-1,2,4-triazine-3,5(2H,4)-dione;

2-[3,5-dichloro-4-[1-methyl-1-[4-phenyl-5-(3-pyridinyl)-2-thiazolyl]ethyl]phenyl]-1,2,4-triazine-3,5(2H,4H)-dione;

2-[3,5-dichloro-4-[1-methyl-1-[4-phenyl-5-(phenylmethyl)-2-thiazolyl]ethyl]-phenyl]-1,2,4-triazine-3,5(2H,4H)-dione;

2-[3,5-dichloro-4-[1-methyl-1-[5-(4-pyridinyl)-1,2,4-oxadiazol-3-yl]ethyl]phenyl]-1,2,4-triazine-3,5(2H,4H)-dione;

2-[3,5-dichloro-4-[1-methyl-1-[4-(3-thienyl)-2-thiazolyl]ethyl]phenyl]-1,2,4-triazine-3,5(2H,4H)-dione;

2-[3,5-dichloro-4-[1-4-(2-furanyl)-2-thiazolyl]-1-methylethyl]phenyl]-1,2,4-triazine-3,5(2H,4H)-dione;

2-[3,5-dichloro-4-[1-methyl-1-[5-(3-pyridinyl)-1,2,4-oxadiazol-3-yl]ethyl]phenyl]-1,2,4-triazine-3,5(2H,4H)-dione;

2-[3,5-dichloro-4-[1-methyl-1-[5-(2-methyl-3-pyridinyl)-1,2,4-oxadiazol-3-yl]ethyl]phenyl]-1,2,4-triazine-3,5(2H,4H)-dione; or 2-[3,5-dichloro-4-[1-methyl-1-(5-phenyl-1,3,4-oxadiazol-2-yl)ethyl]phenyl]-1,2,4-triazine-3,5(2H,4H)dione; or a N-oxide, a pharmaceutically acceptable addition salt or a stereochemically isomeric form thereof.

4. A compound as claimed in claim 1 provided that in those compounds wherein X is a direct bond, at least one of R³ and R⁴ is hydrogen, and R² is 3-pyridinyl optionally substituted in the 6 position with an optionally substituted alkyl or acyl group are excluded.

5. A compound as claimed in claim 2 provided that in those compounds wherein X is a direct bond, at least one of R³ and R⁴ is hydrogen, and R² is 3-pyridinyl optionally substituted in the 6 position with an optionally substituted alkyl or acyl group re excluded.

6. A compound as claimed in claim 1 wherein the 6-azauracil moiety is in the para position relative to the carbon atom bearing the —X—R², R³ and R⁴ substituents.

7. A compound as claimed in claim 2 wherein the 6-azauracil moiety is in the para position relative to the carbon atom bearing the —X—R², R³ and R⁴ substituents.

8. A compound as claimed in claim 4 wherein the 6-azauracil moiety is in the para position relative to the carbon atom bearing the —X—R², R³ and R⁴ substituents.

9. A compound as claimed in claim 5 wherein the 6-azauracil moiety is in the para position relative to the carbon atom bearing the —X—R², R³ and R⁴ substituents.

10. A compound as claimed in claim 1 wherein R² is a monocyclic heterocycle selected from the group consisting of: pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, wherein said monocyclic heterocycles each independently may optionally be substituted with one, or where possible, two or three substituents each independently elected from Het², R¹¹ and $C_{1-4}$alkyl optionally substituted with Het² or R¹¹.

11. A compound as claimed in claim 2 wherein R² is a monocyclic heterocycle selected from the group consisting of: pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, wherein said monocyclic heterocycles each independently may optionally be substituted with one, or where possible, two or three substituents each independently selected from Het², R¹¹ and $C_{1-4}$alkyl optionally substituted with Het² or R¹¹.

12. A compound as claimed in claim 4 wherein R² is a monocyclic heterocycle selected from the group consisting of: pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, wherein said monocyclic heterocycles each independently may optionally be substituted with one, or where possible, two or three substituents each independently selected from Het², R¹¹ and $C_{1-4}$alkyl optionally substituted with Het² or R¹¹.

13. A compound as claimed in claim 5 wherein R² is a monocyclic heterocycle selected from the group consisting of: pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, wherein said monocyclic heterocycles each independently may optionally be substituted with one, or where possible, two or three substituents each independently elected from Het², R¹¹ and $C_{1-4}$alkyl optionally substituted with Het² or R¹¹.

14. A compound as claimed in claim 6 wherein $R^2$ is a monocyclic heterocycle selected from the group consisting of: pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, wherein said monocyclic heterocycles each independently may optionally be substituted with one, or where possible, two or three substituents each independently elected from $Het^2$, $R^{11}$ and $C_{1-4}$alkyl optionally substituted with $Het^2$ or $R^{11}$.

15. A compound as claimed in claim 7 wherein $R^2$ is a monocyclic heterocycle selected from the group consisting of: pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, wherein said monocyclic heterocycles each independently may optionally be substituted with one, or where possible, two or three substituents each independently selected from $Het^2$, $R^{11}$ and $C_{1-4}$alkyl optionally substituted with $Het^2$ or $R^{11}$.

16. A compound as claimed in claim 8 wherein $R^2$ is a monocyclic heterocycle selected from the group consisting of: pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, wherein said monocyclic heterocycles each independently may optionally be substituted with one, or where possible, two or three substituents each independently selected from $Het^2$, $R^{11}$ and $C_{1-4}$alkyl optionally substituted with $Het^2$ or $R^{11}$.

17. A compound as claimed in claim 9, wherein $R^2$ is a monocyclic heterocycle selected from the group consisting of: pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, wherein said monocyclic heterocycles each independently may optionally be substituted with one, or where possible, two or three substituents each independently elected from $Het^2$, $R^{11}$ and $C_{1-4}$alkyl optionally substituted with $Het^2$ or $R^{11}$.

18. A compound as claimed in claim 1 wherein $R^3$ and $R^4$ are both methyl and —X—$R^2$ is $Het^1$.

19. A compound as claimed in claim 2 wherein $R^3$ and $R^4$ are both methyl and —X—$R^2$ is $Het^1$.

20. A compound as claimed in claim 4 wherein $R^3$ and $R^4$ are both methyl and —X—$R^2$ is $Het^1$.

21. A compound as claimed in claim 5 wherein $R^3$ and $R^4$ are both methyl and —X—$R^2$ is $Het^1$.

22. A compound as claimed in claim 6 wherein $R^3$ and $R^4$ are both methyl and —X—$R^2$ is $Het^1$.

23. A compound as claimed in claim 7 wherein $R^3$ and $R^4$ are both methyl and —X—$R^2$ is $Het^1$.

24. A compound as claimed in claim 8 wherein $R^3$ and $R^4$ are both methyl and —X—$R^2$ is $Het^1$.

25. A compound as claimed in claim 9 wherein $R^3$ and $R^4$ are both methyl and —X—$R^2$ is $Het^1$.

26. A compound as claimed in claim 10 wherein $R^3$ and $R^4$ are both methyl and —X—$R^2$ is $Het^1$.

27. A compound as claimed in claim 11 wherein $R^3$ and $R^4$ are both methyl and —X—$R^2$ is $Het^1$.

28. A compound as claimed in claim 12 wherein $R^3$ and $R^4$ are both methyl and —X—$R^2$ is $Het^1$.

29. A compound as claimed in claim 13 wherein $R^3$ and $R^4$ are both methyl and —X—$R^2$ is $Het^1$.

30. A compound as claimed in claim 14 wherein $R^3$ and $R^4$ are both methyl and —X—$R^2$ is $Het^1$.

31. A compound as claimed in claim 15 wherein $R^3$ and $R^4$ are both methyl and —X—$R^2$ is $Het^1$.

32. A compound as claimed in claim 16 wherein $R^3$ and $R^4$ are both methyl and —X—$R^2$ is $Het^1$.

33. A compound as claimed in claim 17 wherein $R^3$ and $R^4$ are both methyl and —X—$R^2$ is $Het^1$.

34. A compound as claimed in claim 1 wherein p is 1 or 2 and each $R^1$ is chloro.

35. A compound as claimed in claim 2 wherein p is 1 or 2 and each $R^1$ is chloro.

36. A compound as claimed in claim 4 wherein p is 1 or 2 and each $R^1$ is chloro.

37. A compound as claimed in claim 5 wherein p is 1 or 2 and each $R^1$ is chloro.

38. A compound as claimed in claim 6 wherein p is 1 or 2 and each $R^1$ is chloro.

39. A compound as claimed in claim 7 wherein p is 1 or 2 and each $R^1$ is chloro.

40. A compound as claimed in claim 8 wherein p is 1 or 2 and each $R^1$ is chloro.

41. A compound as claimed in claim 9 wherein p is 1 or 2 and each $R^1$ is chloro.

42. A compound as claimed in claim 10 wherein p is 1 or 2 and each $R^1$ is chloro.

43. A compound as claimed in claim 11 wherein p is 1 or 2 and each $R^1$ is chloro.

44. A compound as claimed in claim 12 wherein p is 1 or 2 and each $R^1$ is chloro.

45. A compound as claimed in claim 13 wherein p is 1 or 2 and each $R^1$ is chloro.

46. A compound as claimed in claim 14 wherein p is 1 or 2 and each $R^1$ is chloro.

47. A compound as claimed in claim 15 wherein p is 1 or 2 and each $R^1$ is chloro.

48. A compound as claimed in claim 16 wherein p is 1 or 2 and each $R^1$ is chloro.

49. A compound as claimed in claim 15 wherein p is 1 or 2 and each $R^1$ is chloro.

50. A compound as claimed in claim 1 wherein $R^3$ and $R^4$ are both methyl, —X—$R^2$ is optionally substituted 2-thiazolyl or 3-oxadiazolyl, the 6-azauracil moiety is in the para position relative to the carbon atom bearing the —X—$R^2$, $R^3$ and $R^4$ substituents, and p is 2 whereby both $R^1$ substituents are chloro positioned ortho relative to the carbon atom bearing the —X—$R^2$, $R^3$ and $R^4$ substituents.

51. A compound as claimed in claim 2 wherein $R^3$ and $R^4$ are both methyl, —X—$R^2$ is optionally substituted 2-thiazolyl or 3-oxadiazolyl, the 6-azauracil moiety is in the para position relative to the carbon atom bearing the —X—$R^2$, $R^3$ and $R^4$ substituents, and p is 2 whereby both $R^1$ substituents are chloro positioned ortho relative to the carbon atom bearing the —X—$R^2$, $R^3$ and $R^4$ substituents.

52. A compound having the formula

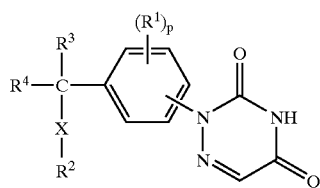

(I)

a N-oxide, a pharmaceutically acceptable addition salt or a stereochemically isomeric form thereof, wherein:

p represents an integer being 0, 1 or 2;

X represents O, S, $NR^5$ or direct bond;

Y represents O, S, $NR^5$, or $S(O)_2$;

each $R^1$ independently represents chloro or trifluoromethyl;

$R^2$ represents $Het^1$ or $C_{1-6}$alkyl substituted with one or two substituents selected from hydroxy, cyano, amino, mono- or di($C_{1-4}$alkyl)amino, $C_{1-6}$alkyloxy, $C_{1-6}$alkylsulfonyloxy, $C_{1-6}$alkyloxycarbonyl, $C_{3-7}$cycloalkyl, aryl, aryloxy, arylthio, $Het^1$, $Het^1$oxy and $Het^1$thio; and if X is O, S or $NR^5$, then $R^2$ may also represent aminocarbonyl, aminothiocarbonyl, $C_{1-4}$alkylcarbonyl, $C_{1-4}$alkylthiocarbonyl, arylcarbonyl, arylthiocarbonyl, $Het^1$carbonyl or $Het^1$thiocarbonyl;

$R^3$ represents hydrogen, $C_{1-6}$alkyl or $C_{3-7}$cycloalkyl;

$R^4$ represents hydrogen, $C_{1-6}$alkyl or $C_{3-7}$cycloalkyl; or $R^3$ and $R^4$ taken together form a $C_{2-6}$alkanediyl;

$R^5$ represents hydrogen or $C_{1-4}$alkyl;

each $R^6$ independently represents $C_{1-6}$alkylsulfonyl, aminosulfonyl, mono- or di($C_{1-4}$alkyl)aminosulfonyl, mono- or di(benzyl)aminosulfonyl, polyhalo$C_{1-6}$alkylsulfonyl, $C_{1-6}$alkylsulfinyl, phenyl$C_{1-4}$alkylsulfonyl, piperazinylsulfonyl, aminopiperidinylsulfonyl, piperidinylaminosulfonyl, N-$C_{1-4}$alkyl-N-piperidinylaminosulfonyl or mono-or di($C_{1-4}$alkyl)amino$C_{1-4}$alkylsulfonyl;

each $R^7$ and each $R^8$ are independently selected from hydrogen, $C_{1-4}$alkyl, hydroxy$C_{1-4}$alkyl, dihydroxy$C_{1-4}$alkyl, aryl, aryl$C_{1-4}$alkyl, $C_{1-4}$alkyloxy$C_{1-4}$alkyl, $C_{1-4}$alkylcarbonyl, aminocarbonyl, arylcarbonyl, $Het^3$carbonyl, $C_{1-4}$alkylcarbonyloxy-$C_{1-4}$alkylcarbonyl, hydroxy$C_{1-4}$alkylcarbonyl, $C_{1-4}$alkyloxycarbonylcarbonyl, mono- or di($C_{1-4}$alkyl) amino$C_{1-4}$alkyl, arylaminocarbonyl, arylaminothiocarbonyl, $Het^3$aminocarbonyl, $Het^3$aminothiocarbonyl, $C_{3-7}$cycloalkyl, pyridinyl$C_{1-4}$alkyl, $C_{1-4}$alkanediyl-C(=O)—O—$R^{14}$, —C(=O)—O—$R^{14}$, —Y—$C_{1-4}$alkanediyl-C(=O)—O—$R^{14}$, $Het^3$, $Het^4$ and $R^6$;

$R^9$ and $R^{10}$ are each independently selected from hydrogen, $C_{1-4}$alkyl, hydroxy$C_{1-4}$alkyl, dihydroxy$C_{1-4}$alkyl, phenyl, phenyl$C_{1-4}$alkyl, $C_{1-4}$alkyloxy$C_{1-4}$ alkyl, $C_{1-4}$alkylcarbonyl, aminocarbonyl, phenylcarbonyl, $Het^3$carbonyl, $C_{1-4}$alkylcarbonyloxy$C_{1-4}$alkylcarbonyl, hydroxy$C_{1-4}$ alkylcarbonyl, $C_{1-4}$alkyloxycarbonylcarbonyl, mono- or di($C_{1-4}$alkyl) amino$C_{1-4}$alkyl, phenylaminocarbonyl, phenylaminothiocarbonyl, $Het^3$aminocarbonyl, $Het^3$aminothiocarbonyl, $C_{3-7}$cycloalkyl, pyridinyl$C_{1-4}$alkyl, $C_{1-4}$alkanediyl-C(=O)—O—$R^{14}$, —C(=O)—O—$R^{14}$, —Y—$C_{1-4}$alkanediyl-C(=O)—O—$R^{14}$, $Het^3$, $Het^4$ and $R^6$;

each $R^{11}$ independently being selected from hydroxy, cyano, nitro, halo, $C_{1-4}$alkyloxy, formyl, $NR^7R^8$, C(=O) $NR^7R^8$, —C(=O)—O—$R^{14}$, aryl, arylcarbonyl, $Het^3$ and C(=O)$Het^3$;

each $R^{14}$ independently represents hydrogen, $C_{1-4}$alkyl, $C_{3-7}$cycloalkyl, aminocarbonylmethylene or mono-or di($C_{1-4}$alkyl)aminocarbonylmethylene;

aryl represents phenyl optionally substituted with one, two or three substituents each independently selected from nitro, azido, cyano, halo, hydroxy, $C_{1-4}$alkyl, $C_{3-7}$cycloalkyl, $C_{1-4}$alkyloxy, formyl, polyhalo$C_{1-4}$alkyl, $NR^9R^{10}$, C(=O)$NR^9R^{10}$, C(=O)—O—$R^{14}$, $R^6$, —O—$R^6$ phenyl, $Het^3$, C(=O)$Het^3$ and $C_{1-4}$alkyl substituted with hydroxy, $C_{1-4}$alkyloxy, C(=O)—O—$R^{14}$, —Y—$C_{1-4}$alkanediyl-C(=O)—O—$R^{14}$, $Het^3$ or $NR^9R^{10}$;

$Het^1$ represents a heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, wherein said monocyclic heterocycles each independently may optionally be substituted with one, or where possible, two or three substituents each independently selected from $Het^2$, $R^{11}$ and $C_{1-4}$alkyl optionally substituted with $Het^2$ or $R^{11}$; provided $Het^1$ is other than 2-substituted-pyridin-5-yl;

$Het^2$ represents a heterocycle selected from furanyl, thienyl, pyridinyl or benzothienyl, wherein said aromatic heterocycles each independently may optionally be substituted with one, or where possible, two or three substituents each independently selected from $Het^4$, $R^{11}$ and $C_{1-4}$alkyl optionally substituted with $R^{11}$;

$Het^3$ represents a monocyclic heterocycle selected from piperidinyl, piperazinyl, morpholinyl and tetrahydropyranyl each independently and optionally substituted with, where possible, one, two, three or four substituents each independently selected from hydroxy, $C_{1-4}$alkyl, C(=O)—O—$R^{14}$, $C_{1-4}$alkylcarbonyl, $R^6$, piperidinyl and $C_{1-4}$alkyl substituted with one or two substituents independently selected from hydroxy, $C_{1-4}$alkyloxy, C(=O)—O—$R^{14}$ and phenyl;

$Het^4$ represents a monocyclic heterocycle selected from thienyl or pyridinyl.

53. A compound a claimed in claim 52, wherein when X is a direct bond, at least one of $R^3$ and $R^4$ is hydrogen, and $R^2$ is 3-pyridinyl, then $R^2$ is not substituted in the 6 position with an optionally substituted alkyl or acyl group.

54. A compound a claimed in claim 52 wherein the 6-azauracil moiety is in the para position relative to the carbon atom bearing the —X—$R^2$, $R^3$ and $R^4$ substituents.

55. A compound a claimed in claim 52 wherein $R^2$ is a monocyclic heterocycle selected from the group consisting of: pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, wherein said monocyclic heterocycles each independently may optionally be substituted with one, where possible, two or three substituents each independently selected from $Het^2$, $R^{11}$ and $C_{1-4}$alkyl optionally substituted with $Het^2$ or $R^{11}$.

56. A compound a claimed in claim 52 wherein $R^3$ and $R^4$ are both methyl and —X—$R^2$ is $Het^1$.

57. A compound a claimed in claim 52 wherein p is 1 or 2 and each $R^1$ is chloro.

58. A compound a claimed in claim 52 wherein $R^3$ and $R^4$ are both methyl, —X—$R^2$ is optionally substituted 2-thiazolyl or 3-oxadiazolyl, the 6-azauracil moiety is in the para position relative to the carbon atom bearing the —X—$R^2$, $R^3$ and $R^4$ substituents, and p is 2 whereby both $R^1$ substituents are chloro positioned ortho relative to the carbon atom bearing the —X—$R^2$, $R^3$ and $R^4$ substituents.

59. A composition comprising a pharmaceutically acceptable carrier and, as active ingredient, a therapeutically effective amount of a compound as claimed in claim 1.

* * * * *